United States Patent
Belcher et al.

(10) Patent No.: US 11,896,633 B2
(45) Date of Patent: Feb. 13, 2024

(54) HOMOGENEOUS ENGINEERED PHAGE POPULATIONS

(71) Applicant: Massachusetts Institute of Technology, Cambridge, MA (US)

(72) Inventors: Angela M. Belcher, Lexington, MA (US); Uyanga Tsedev, Somerville, MA (US); Fred Lam, Brookline, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 246 days.

(21) Appl. No.: 17/208,256

(22) Filed: Mar. 22, 2021

(65) Prior Publication Data
US 2021/0205381 A1 Jul. 8, 2021

Related U.S. Application Data

(63) Continuation of application No. 16/040,793, filed on Jul. 20, 2018, now Pat. No. 10,987,388.

(60) Provisional application No. 62/535,604, filed on Jul. 21, 2017.

(51) Int. Cl.
| | |
|---|---|
| A61K 35/76 | (2015.01) |
| A61K 47/69 | (2017.01) |
| A61K 47/64 | (2017.01) |
| A61K 9/00 | (2006.01) |
| C12N 7/00 | (2006.01) |
| C12N 15/70 | (2006.01) |
| C12N 15/861 | (2006.01) |
| A61K 49/00 | (2006.01) |

(52) U.S. Cl.
CPC .......... *A61K 35/76* (2013.01); *A61K 47/6901* (2017.08); *C12N 7/00* (2013.01); *C12N 15/70* (2013.01); *C12N 15/861* (2013.01); *A61K 9/0019* (2013.01); *A61K 47/6415* (2017.08); *A61K 49/0021* (2013.01); *C12N 2795/14121* (2013.01); *C12N 2795/14122* (2013.01); *C12N 2795/14131* (2013.01); *C12N 2795/14132* (2013.01); *C12N 2800/202* (2013.01); *C12N 2810/40* (2013.01)

(58) Field of Classification Search
None
See application file for complete search history.

(56) References Cited

U.S. PATENT DOCUMENTS

| | | |
|---|---|---|
| 2003/0113714 A1 | 6/2003 | Belcher et al. |
| 2006/0275791 A1 | 12/2006 | Belcher et al. |
| 2012/0003629 A9 | 1/2012 | Belcher et al. |
| 2013/0230464 A1 | 9/2013 | Yi et al. |
| 2014/0030697 A1 | 1/2014 | Ploegh et al. |
| 2017/0017069 A1 | 1/2017 | Siegel et al. |

FOREIGN PATENT DOCUMENTS

EP  0 805 877 B1  8/2001

OTHER PUBLICATIONS

Benzinger et al., "Infectious Nucleic Acids of *Escherichia coli* Bacteriophages," European J. Biochem., 1967, 2:414-428.
Bernard et al., "Chemical strategies for the covalent modification of filamentous phage," Frontiers in Microbiology, Dec. 23, 2014, 5(734):1-7.
Chen et al., "Assembly of Viral Hydrogels for Three-Dimensional Conducting Nanocomposites," Advanced Materials, 2014, 26:5101-5107.
Courchesne et al., "Assembly of a Bacteriophage-Based Template for the Organization of Materials into Nanoporous Networks," Advanced Materials, 2014, 26:3398-3404.
Dang et al., "Layer-by-layer assembled fluorescent probes in the second near-infrared window for systemic delivery and detection of ovarian cancer," PNAS, May 10, 2016, 113(19):5179-5184.
Dotto et al., "Initiation and termination of phage f1 plus-strand synthesis," Proc. Nat. Acad. Sci. USA, Dec. 1982, 79:7122-7126.
Flynn et al., "Viruses as vehicles for growth, organization and assembly of materials," Acta Materialia, 2003, 51:5867-5880.
Geng et al., "Shape effects of filaments versus spherical particles in flow and drug delivery," Nature Nanotechnology, Apr. 2007, 2:249-255.
Gentile et al., "The effect of shape on the margination dynamics of non-neutrally buoyant particles in two-dimensional shear flows," Journal of Biomechanics, 2008, 41(10):2312-2318.
Ghosh et al., "Deep, noninvasive imaging and surgical guidance of submillimeter tumors using targeted M13-stabilized single-walled carbon nanotubes," PNAS, Sep. 23, 2014, 111(38):13948-13953.
Ghosh et al., "Refactored M13 Bacteriophage as a Platform for Tumor Cell Imaging and Drug Delivery," ACS Synthetic Biology, 2012, 1:576-582.
Griffith et al., "Mini M13 Bacteriophage: Circular Fragments of M13 DNA are Replicated and Packaged during Normal Infections," Virology, 1974, 59:139-152.
Hagens et al., "Genetically modified filamentous phage as bactericidal agents: a pilot study," Letters in Applied Microbiology, 2003, 37:318-323.
Hess et al., "M13 Bacteriophage Display Framework That Allows Sortase-Mediated Modification of Surface-Accessible Phage Proteins," Bioconjugate Chemistry, 2012, 23:1478-1487.
Hess et al., "Orthogonal Labeling of M13 Minor Capsid Proteins with DNA to Self-Assemble End-to-End Multiphage Structures," ACS Synthetic Biology, May 28, 2013, 2:490-496.

(Continued)

*Primary Examiner* — Nicole Kinsey White
(74) *Attorney, Agent, or Firm* — Foley & Lardner LLP

(57) ABSTRACT

Provided are engineered phages populations, which are homogeneous in length, as well as methods of making and methods of using such phages. Also provided are engineered chlorotoxin-phages as well as their methods of making and using. The disclosed homogeneous phage populations and chlorotoxin-phages may be used, for example, for treating and/or imaging tumors, such as central nervous system tumors.

43 Claims, 23 Drawing Sheets
(23 of 23 Drawing Sheet(s) Filed in Color)
Specification includes a Sequence Listing.

(56) References Cited

OTHER PUBLICATIONS

Hewitt et al., "Miniphage—a Class of Satellite Phage to M13," Journal General Virology, 1975, 26:87-94.

Horiuchi et al., "Initiation mechanism in replication of filamentous phage DNA," Genes to Cells, 1997, 2:425-432.

Huang et al., "Programmable Assembly of Nanoarchitectures Using Genetically Engineered Viruses," Nano Letters, 2005, 5(7):1429-1434.

International Search Report and Written Opinion dated Jan. 9, 2018, in PCT/JP2017/043298.

Jin et al., "Collagen mimetic peptide engineered M13 bacteriophage for collagen targeting and imaging in cancer," Biomaterials, 2014, 35:9236-9245.

Krishnan et al., "A Bacteriophage Capsid Protein Provides a General Amyloid Interaction Motif (GAIM) That Binds and Remodels Misfolded Protein Assemblies," J. Mol. Biol., 2014, 426:2500-2519.

Messing et al., "Phage M13 for the treatment of Alzheimer and Parkinson disease," Gene, 2016, 583:85-89.

Pires et al., "Genetically Engineered Phages: a Review of Advances over the Last Decade," Microbiology and Molecular Biology Reviews, Sep. 2016, 80(3):523-543.

Pope et al., "Cluster K Mycobacteriophages: Insights into the Evolutionary Origins of Mycobacteriophage TM4," Plos One, 2011, 6(10):e26750, 22 pages.

Smith et al., "Shape Matters: Intravital Microscopy Reveals Surprising Geometrical Dependence for Nanoparticles in Tumor Models of Extravasation," Nano Letters, 2012, 12:3369-3377.

Sorokin et al., "A New Approach Using Multiplex Long Accurate PCR and Yeast Artificial Chromosomes for Bacterial Chromosome Mapping and Sequencing," Genome Research, 1996, 6:448-453.

Specthrie et al., "Construction of a Microphage Variant of Filamentous Bacteriophage," J. Mol. Biol., 1992, 228:720-724.

Stroud et al., "In Vivo Bio-imaging Using Chlorotoxin-based Conjugates," Current Pharm Des., 2011, 17(38):4362-4371.

Toy et al., "Shaping cancer nanomedicine: the effect of particle shape on the in vivo journey of nanoparticles," Nanomedicine, 2014, 9(1): 121-134.

Tsedev, Uyanga, "Engineering M13 Bacteriophage Platforms for Cancer Therapy Applications," Massachusetts of Technology, Jun. 2015, 48 pages.

Veiseh et al., "Specific Targeting of Brain Tumors with an Optical/Magnetic Resonance Imaging Nanoprobe across the Blood-Brain Barrier," Cancer Res., 2009, 69(15):6200-6207.

Yi et al., "M13 Phage-Functionalized Single-Walled Carbon Nanotubes As Nanoprobes for Second Near-Infrared Window Fluorescence Imaging of Targeted Tumors," Nano letters, 2012, 12(3):1176-1183.

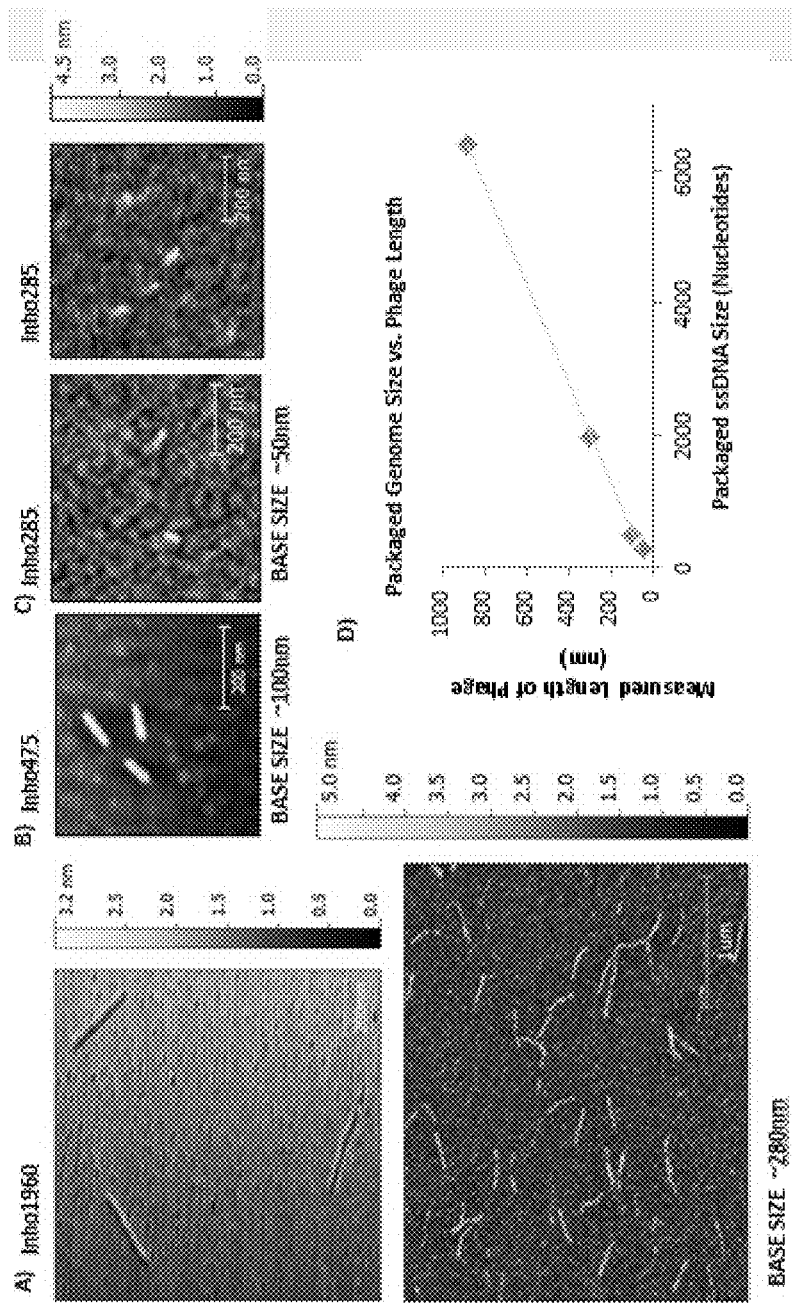

Figure 4

```
         ←p3
5' TTAGTGGTACCTTTCTATTCTCACTCTATGTGCATGCCGTGCTTTACCACCGATC
3' AATCACCATGGAAAGATAAGAGTGAGATACACGTACGGCACGAAATGGTGGCTAG

[Chlorotoxin Sequence]

ATCAGATGGCGCGCAAATGCGATGATTGCTGCGGGCAAAGGCCGGCAAATG
   TAGTCTACCGCGCGTTTACGCTACTAACGACGCCCGTTTCCGGCCGTTTAC
   CTATGGCCCGCAGTGCCTGTGCCGCTCGGCCGAAACT 3'
   GATACCGGGCGTCACGGACACGGCCGAGCCGGCTTTGA 5'
                                     p3→
```

Figure 9

| Phage | WT | inho1960 | inho1960 |
|---|---|---|---|
| CTX | | | |
| DSPH | 2e12pfu injection | 2e12pfu injection | 2e12pfu injection |
| CNT | >50,000 tumor BLI | 8,000 tumor BLI | 8,000 tumor BLI |
| NIRII | | | |

| Phage | inho1960 | inho1960 | inho1960 |
|---|---|---|---|
| CTX | | | |
| DSPH | 1.2e13pfu injection | 1.8e13pfu injection | 1.8e13pfu injection |
| CNT | 30,000 tumor BLI | 12,000 tumor BLI | >50,000 tumor BLI |
| NIRII | | | |

Figure 14 f1 Origin of Replication Site [Part of Removed sequence]

5' CCATCGCCCTGATAGACGGTTTTTCGCCCTTTGACGTTGGCTTTAAT
3' GGTAGCGGGACTATCTGCCAAAAAGCGGGAAACTGCAACCGAAATTA

AGTGGACTCTTGTTCCAAACTGGAACAACACTCAACCCTATCTCGGGC 3'
TCACCTGAGAACAAGGTTTGACCTTGTTGTGAGTTGGGATAGAGCCCG 5'

Figure 16

Modified f1 Origin of Replication Site

5'    CCATCGCCCTGATAGACGGTTTTTCGCCCTTTGACGTTGGCTTTAAT
3'    GGTAGCGGGACTATCTGCCAAAAAGCGGGAAACTGCAACCGAAATTA

AGTGGACTCTTGTTCCAAACTGGAACAACACTCAACCCTATCTCGGGC 3'
TCACCTGAGAACAAGGTTTGACCTTGTTGTGAGTTGGGATAGAGCCCG 5'

*As mentioned in Douto et al., PNAS (1982)

f1 Origin of Replication Site Modified for Termination V.1

5'    GGCCATCGCCCTGATAGACGGTTTTTCGCCCTTTGACGTTGG
3'    CCGGTAGCGGGACTATCTGCCAAAAAGCGGGAAACTGCAACC

AGTCCACGTTCTTTAATAGTGGACTCTTGTTCCAAACAACACT 3'
TCAGGTGCAAGAAATTATCACCTGAGAACAAGGTTTGTTGTGA 5'

*As mentioned in Horiuchi, Genes to Cells (1997)

f1 Origin of Replication Site Modified for Termination V.2

5'    GGCCATCGCCCTGATAGACGGTTTTTCGCCCTTTGACGTTGG
3'    CCGGTAGCGGGACTATCTGCCAAAAAGCGGGAAACTGCAACC

AGTCCACGTTCTTTAATAGTGGACTCTTAACTGGAACAACACT 3'
TCAGGTGCAAGAAATTATCACCTGAGAATTGACCTTGTTGTGA 5'

*As mentioned in Horiuchi, Genes to Cells (1997)

Packaging Signal Sequence

5'    CGCGCCCTGTAGCGGCGCATTAAGCGCGGCGGGTGTGGTGGT
3'    GCGCGGGACATCGCCGCGTAATTCGCGCCGCCCACCACCA

TACGCGCAGCGTGACCGCTACACTTGCCAGCGCCCTAGCGCCCGCTCC 3'
ATGCGCGTCGCACTGGCGATGTGAACGGTCGCGGGATCGCGGGCGAGG 5'

Figure 23

M13 Bacteriophage Assembly Proteins

| Phage Protein | Function | # of Amino Acids | MW (Daltons) |
|---|---|---|---|
| P2 | DNA replication | 410 | 46,137 |
| P10 | DNA replication | 111 | 12,672 |
| P5 | binding of ssDNA | 87 | 9,682 |
| P8 | major coat capsid | 50 | 5,235 |
| P3 | minor tail capsid | 406 | 42,522 |
| P6 | minor tail capsid | 112 | 12,342 |
| P7 | minor head capsid | 33 | 3,599 |
| P9 | minor head capsid | 32 | 3,650 |
| P1 | assembly | 348 | 39,502 |
| P4 | assembly | 405 | 43,502 |
| P11 | assembly | 108 | 12,424 |

HOMOGENEOUS ENGINEERED PHAGE POPULATIONS

CROSS-REFERENCE TO RELATED APPLICATIONS

This application is a Continuation of U.S. application Ser. No. 16/040,793, filed Jul. 20, 2018, which claims priority from U.S. Provisional Application No. 62/535,604, filed Jul. 21, 2017, the entire contents of which are incorporated by reference herein.

STATEMENT OF GOVERNMENT SUPPORT

This invention was made with Government support under Grant No. P30 CA014051 awarded by the National Institutes of Health. The Government has certain rights in the invention.

The instant application contains a Sequence Listing which has been submitted in ASCII format via EFS-WEB and is hereby incorporated by reference in its entirety. Said ASCII copy, created on Mar. 19, 2021, is named sequence.txt and is 2,432 bytes.

FIELD

The present application relates generally to the field of biotechnology and more specifically to engineered bacteriophage systems and methods of making and using them.

SEQUENCE LISTING

The instant application contains a Sequence Listing which has been submitted electronically in ASCII format and is hereby incorporated by reference in its entirety. Said ASCII copy, created on Jul. 19, 2018, is named sequence.txt and is 3 KB in size.

SUMMARY

One embodiment is a method of making a homogeneous phage population and/or a homogeneous ssDNA population, comprising: obtaining a first artificial plasmid comprising an f1 origin replication sequence; obtaining a second artificial plasmid that does not comprise an f1 origin replication sequence; and co-transforming the first artificial plasmid and the second artificial plasmid into a bacterial strain to produce a homogeneous phage population and/or a homogeneous ssDNA population, wherein the first and second artificial plasmid together contain sequences encoding a complete library of phage coat and assembly proteins.

Another embodiment is a homogeneous engineered phage population, wherein at least 30% of phages in the phage population have a length within 15% of a length value, which is selected from 10 nm to 10 microns.

Yet another embodiment is a homogeneous engineered phage population, wherein at least 30% of phages in the phage population have a length within 8 nm of a length value, which is selected from 10 nm to 10 microns.

Yet another embodiment is a phage comprising chlorotoxin expressed by a coat protein of the phage.

Yet another embodiment is a kit for making a homogeneous phage population and/or a homogeneous ssDNA population comprising: a first artificial plasmid comprising an f1 origin replication sequence; and a second artificial plasmid, which does not comprise an f1 origin replication sequence, wherein the first and second artificial plasmid together contain sequences encoding a complete library of phage coat and assembly proteins.

BRIEF DESCRIPTION OF THE DRAWINGS

The application file contains at least one drawing executed in color. Copies of this patent application publication with color drawing(s) will be provided by the Office upon request and payment of the necessary fee.

FIG. 3A-C are atomic force microscopy (AFM) images of inho 1960, inho 475 and inho 285 phages. FIG. 3D is a plot showing a measured length of phage in nm as a function of packaged ssDNA size.

FIG. 4 shows a nucleotide sequence (SEQ ID No. 1) for M13 code modified with chlorotoxin sequence at the p3 gene.

FIG. 9 relates to the use of CTX phage (long and short) with NIRII imaging of glioma (ex-vivo, post IV injection).

FIG. 14 shows a replication sequence from M13-ori (SEQ ID No. 2).

FIG. 16 shows sequences of f1 replication modified for origin only (SEQ ID No. 3), termination only (SEQ ID No. 4 and SEQ ID No. 5), and the packaging signal as found in M13-ori (SEQ ID No. 6).

FIG. 23 provides a list of M13 bacteriophage proteins.

DETAILED DESCRIPTION

Figure 1:
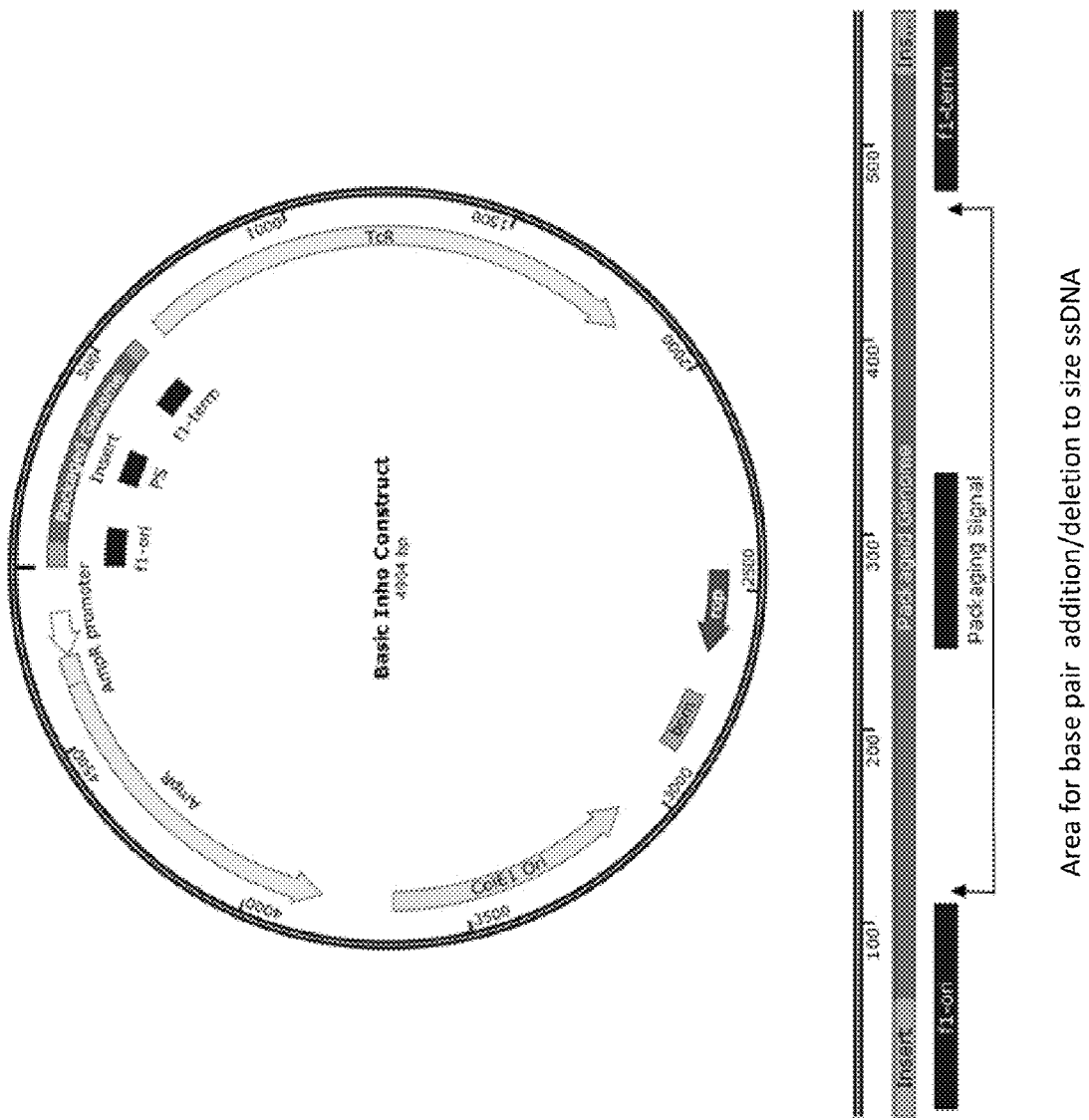
FIG. 1 is an Inho construct plasmid map, with site of circular ssDNA production region shown in dark green.

Unless otherwise specified, "a" or "an" refers to one or more.

The present inventors developed a method of producing homogeneous phage populations. The method may be applied to a phage with an isolatable packaging signal sequence. In some embodiments, a phage may be a filamentous phage. Examples of filamentous phages include Ff phages, such as M13 bacteriophage, Ike phage, f1 phage and fd phage. Yet in other embodiments, a phage may be a non-filamentous phage, such as lambda phage or adeno-associated virus.

The method includes obtaining two artificial, i.e. man-made, phage plasmids and co-transforming the two artificial plasmids into a competent bacterial strain to produce a homogeneous phage population. In some embodiments, the product of the co-transformation may be amplified to produce the homogeneous phage population.

For Ff phages, such as M13 bacteriophage, the bacterial strain may be one that carries the F-episome. In some embodiments, the bacterial strain may be a strain of *E. coli*. For example, the bacterial strain may be DH5a, NovaBlue, XL10, ER2738 or XL1. In some embodiments, the bacterial strain may be an antibiotic resistant strain, such as a tetracycline resistant bacterial strain.

The two artificial plasmids are preferably such that together they contain sequences for a complete library for coat and assembly proteins for a particular type of phage. In other words, the two artificial plasmids contain together at least one copy of each protein encoding gene present in a corresponding wildtype phage genome. For example, for M13 phage, the two artificial plasmids will contain together sequences for each of pI-pXI proteins, see FIG. 23.

The first of the artificial plasmids may be a modified (compared to the wildtype) circular double strand (ds) DNA phage plasmid. The first artificial plasmid may contain an f1 origin replication sequence. The first artificial plasmid may prepared by modifying a wildtype phage plasmid in certain areas. For example, at least 2 base pairs or at least 5 base pairs or at least 10 base pairs or at least 20 base pairs or at least 50 base pairs or at least 100 base pairs or at least 150 base pairs or at least 200 base pairs or at least 250 base pairs or at least 300 base pairs or at least 350 base pairs or at least 400 base pairs or at least 450 base pairs or at least 500 base pairs or at least 600 base pairs or at least 700 base pairs or at least 800 base pairs or at least 900 base pairs or at least 1000 base pairs or at least 1500 base pairs or at least 2000 base pairs or at least 2500 base pairs or at least 3000 base pairs or at least 3500 base pairs or at least 4000 base pairs or at least 4500 base pairs or at least 5000 base pairs or at least 5500 base pairs or at least 6000 base pairs may be added, replaced, and/or removed. The modification(s) of the dsDNA acting as the first plasmid may be used to control or define a length of phages in the phage population and/or a length of produced ssDNA. In some embodiments, the f1 origin replication sequence may also function as an f1 termination replication sequence. Such sequence is illustrated, for example, in FIG. 14. In some embodiments, the first artificial plasmid may also contain at least one of an f1 termination replication sequence and a packaging signal sequence, such as SEQ ID No. 6. In some embodiments, the first artificial plasmid may contain an f1 termination replication sequence in addition to the f1 origin replication. In such case, the ssDNA's producing section between the f1 origin replication sequence and the f1 termination of replication sequence may be modified. For example, one or more base pairs may be added, replaced or removed. In certain embodiments, at least 2 base pairs or at least 5 base pairs or at least 10 base pairs or at least 20 base pairs or at least 50 base pairs or at least 100 base pairs or at least 150 base pairs or at least 200 base pairs or at least 250 base pairs or at least 300 base pairs or at least 350 base pairs or at least 400 base pairs or at least 450 base pairs or at least 500 base pairs or at least 600 base pairs or at least 700 base pairs or at least 800 base pairs or at least 900 base pairs or at least 1000 base pairs or at least 1500 base pairs or at least 2000 base pairs or at least 2500 base pairs or at least 3000 base pairs or at least 3500 base pairs or at least 4000 base pairs or at least 4500 base pairs or at least 5000 base pairs or at least 5500 base pairs or at least 6000 base pairs may be added, replaced or removed.

In some embodiments, the first artificial plasmid may contain an f1 origin replication sequence, a packaging signal sequence and an f1 termination of replication sequence. The packaging signal sequence may comprise SEQ ID NO. 6 (FIG. 16) A) ssDNA producing section between the f1 origin replication sequence and the packaging signal sequence and/or B) ssDNA producing section between the packaging signal sequence and the f1 termination of replication sequence may be modified. For example, one or more bases in one or both of these sections may be added, replaced or removed. In certain embodiments, at least 2 base pairs or at least 5 base pairs or at least 10 base pairs or at least 20 base pairs or at least 50 base pairs or at least 100 base pairs or at least 150 base pairs or at least 200 base pairs or at least 250 base pairs or at least 300 base pairs or at least 350 base pairs or at least 400 base pairs or at least 450 base pairs or at least 500 base pairs or at least 600 base pairs or at least 700 base pairs or at least 800 base pairs or at least 900 base pairs or at least 1000 base pairs or at least 1500 base pairs or at least 2000 base pairs or at least 2500 base pairs or at least 3000 base pairs or at least 3500 base pairs or at least 4000 base pairs or at least 4500 base pairs or at least 5000 base pairs or at least 5500 base pairs or at least 6000 base pairs may be added, replaced or removed in one or both of these sections.

In some embodiments, the first artificial plasmid may contain an f1 origin replication sequence and a packaging signal sequence. The packaging signal sequence may comprise SEQ ID NO. 6 (FIG. 16) A) ssDNA producing section between the end of the f1 origin replication sequence and the packaging signal sequence and/or B) ssDNA producing section between the packaging signal sequence and the start of f1 origin of replication sequence may be modified. For example, one or more base pairs in one or both of these sections may be added, replaced or removed. In certain embodiments, at least 2 base pairs or at least 5 base pairs or at least 10 base pairs or at least 20 base pairs or at least 50 base pairs or at least base pairs or at least 150 base pairs or at least 200 base pairs or at least 250 base pairs or at least 300 base pairs or at least 350 base pairs or at least 400 base pairs or at least 450 base pairs or at least 500 base pairs or at least 600 base pairs or at least base pairs or at least 800 base pairs or at least 900 base pairs or at least 1000 base pairs or at least 1500 base pairs or at least 2000 base pairs or at least 2500 base pairs or at least 3000 base pairs or at least 3500 base pairs or at least 4000 base pairs or at least 4500 base pairs or at least 5000 base pairs or at least 5500 base pairs or at least 6000 base pairs may be added, replaced or removed in one or both of these sections.

The first artificial plasmid leads to the replication of a packageable circular ssDNA, i.e. a plasmid, which may be packaged, after the co-transformation of the first and second artificial plasmids into a bacterial strain.

In some embodiments, the first artificial plasmid may be modified in such a way that it may be missing one or more phage protein genes. In such case, at least one copy of the phage protein missing gene(s) may be present in the second plasmid.

In some embodiments, the first artificial plasmid may be modified in such a way that it may be missing all of phage protein genes. In such case, at least one copy of each phage protein gene may be present in the second plasmid.

In some embodiments, the f1 origin replication sequence may be a modified (compared to the wildtype one) f1 origin replication sequence. A non-limiting example of a modified f1 origin replication sequence is presented in FIG. 16 as SEQ ID No. 3 (Dotto et al., PNAS, 1982, 79(23), 7122-7126).

In some embodiments, the f1 termination of replication sequence may be a modified (compared to the wildtype one) f1 termination of replication sequence. Non-limiting examples of modified f1 termination of replication sequences are presented in FIG. 16 and SEQ ID Nos. 4 and 5 (Horiuchi, Genes to Cells, 1997, 2(7), 425-432).

In some embodiments, the first artificial plasmid may be missing a packaging signal sequence. Such sequence may be used to produce minimal size phage populations and minimal size ssDNA. When the first artificial plasmid is missing a packaging signal sequence, it may be preferred to use the second artificial plasmid, which also misses a packaging signal sequence.

The second of the two artificial plasmids may be a helper phage plasmid, which is modified to disrupt the origin for packageable ssDNA replication.

For example, the second artificial plasmid may be a helper phage plasmid which is modified so that it does not contain an f1 replication origin sequence (either wildtype or modified). In some embodiments, the second artificial plasmid may be a helper phage plasmid which is modified so that it does not also contain a packaging signal sequence (either wildtype or modified).

In some embodiments, other than missing the f1 replication origin sequence and optionally, the packaging signal sequence, the modified helper phage plasmid used as the second artificial plasmid may include all essential phage assembly components, i.e. contain sequences encoding all phage proteins (coat and assembly proteins). In such case, the first plasmid may or may not be missing all these sequences.

The second artificial plasmid may be prepared, for example, from a commercial helper phage plasmid by reassembling the intergenic region to disrupt the origin for packageable ssDNA replication. For example, in some embodiments, a sequence comprising SEQ ID No. 2 may be removed from a helper phage plasmid. Examples of commercially available helper phage plasmids for M13 bacteriophage include M13KE, M13K07 and R 408.

The modified helper phage plasmid used as the second artificial plasmid may include further modifications. For example, COLE1 (p15a-ori) plasmid replication sequence may be included. Such inclusion may allow achieving an optimal copy numbers during bacterial growth, such as *E. coli* growth. The modified helper phage may also include one or more of additional functionalization, such as adding chlorotoxin (CTX) sequence, such as SEQ ID No. 1, at the pIII gene; adding a sequence for DSPH or a sequence for a carbon nanotube complexing peptide at the pVIII gene (Ghosh et al, PNAS 2014 111 (38) 13948-13953); adding a sequence encoding HIS-tag at the pIII gene ((Hess et al, Bioconjug Chem., 2012, 23(7), 1478-1487); separating overlapping capsid sequences (Ghosh et al, ACS Synth Bio., 2012, 1(12), 576-582).

In some embodiments, the product of the co-transformation, which may be a bacterial colony comprising a phage population, may be amplified. For example, a bacterial growth media, such as a lysogeny broth media, may be prepared. The bacterial colony, which may be the product of the co-transformation may be grown in the bacterial growth media to produce a resultant bacterial culture. Then bacteria may be removed from the resultant bacterial culture to produce a supernatant containing a phage product. Such removal may be performed by centrifuging the resultant bacterial culture. The supernatant containing the phage product may be used for precipitating phage particles of the phage population. The phage precipitated phage media may be centrifuged to pellet out the phage phage population. The pelleted phage population may be suspended in a sterile solution, which may be, for example, a sterile buffer, or purified water, such as MilliQ water.

In some embodiments, the product of the co-transformation may be stored for up to three months prior to amplification. For example, the product of the co-transformation may be stored for at least 1 day up to three months or for at least 2 days up to three months or for at least 3 days up to three months or for at least 5 days up to three months or for at least a week up to three months or for at least 10 days up to three months or for at least two weeks up to three months or for at least 3 weeks up to three months or for at least one month up to three months or for at least 45 days up to three months and any values or subranges within these ranges.

The present method may allow production of homogeneous phage populations. A phage population may be homogeneous when a substantial portion of phages of the population, e.g. at least 10% of the population, has a phage length, which is substantially close to a selected phage length value. The selected length value may be determined by selecting a particularly modified first artificial plasmid. In certain embodiments, the selected length value may be determined by selecting a length (and/or a number of base pairs) of the first artificial plasmid. In general, when all other conditions are the same, a longer (having more base pairs) first artificial plasmid will result in a longer phage population, while a shorter (having less base pairs) first artificial plasmid will result in a shorter phage population. For example, artificial plasmids having 1960, 475 and 285 base pairs when co-transformed with the RM13-f1 second plasmid will give phages having lengths of 280 nm, 100 nm and 50 nm.

In some embodiments, at least 10% of phages or at least 20% of phages or at least 30% of phages or at least 40% of phages or at least 50% of phages or at least 60% of phages or at least 70% of phages or at least 80% of phages or at least 90% of phages may be within 20% or within 15% or within 12% or within 10% or within 9% or within 8% or within 7% or within 6% or within 5% of the selected phage length value.

In some embodiments, at least 10% of phages or at least 20% of phages or at least 30% of phages or at least 40% of phages or at least 50% of phages or at least 60% of phages or at least 70% of phages or at least 80% of phages or at least 90% of phages may be within 20 nm or within 15 nm or within 12 nm or within 10 nm or within nm or within 8 nm or within 7 nm or within 6 nm or within 5 nm of the selected phage length value.

The selected phage length value may be, for example, a value between 10 nm and 10000 nm (10 microns). For example, the selected phage length value may be from 10 nm to 8000 nm or from 10 nm to 6000 nm or from 10 nm for 4000 nm or from 10 nm to 3000 nm or from 10 nm to 2000 nm or from 10 nm to 1800 nm or from 10 nm to 1600 nm or from 10 nm to 1400 nm or from 15 nm to 8000 nm or from 15 nm to 6000 nm or from 15 nm for 4000 nm or from 15 nm to 3000 nm or from 15 nm to 2000 nm or from 15 nm to 1800 nm or from 15 nm to 1600 nm or from 15 nm to 1400 nm or from 20 nm to 8000 nm or from 20 nm to 6000 nm or from 20 nm for 4000 nm or from 20 nm to 3000 nm or from 20 nm to 2000 nm or from 20 nm to 1800 nm or from 20 nm to 1600 nm or from 20 nm to 1400 nm.

In some embodiments, the selected phage length value may be below 50 nm. For example, the selected phage length value may be at least 10 nm but less than 50 nm or at least 10 nm but no more than 45 nm or at least 10 nm but no more than 40 nm or at least 10 nm but no more than 35 nm or at least 15 nm but less than 50 nm or at least 15 nm but no more than 45 nm or at least 15 nm but no more than 40 nm or at least 15 nm but no more than 35 nm. In some embodiments, the selected phage length value may be greater than 50 nm. For example, the selected phage length value may be at least 55 nm or at least 60 nm or at least nm or at least 70 nm or at least 75 nm or at least 80 nm or at least 80 nm or at least 85 nm or at least 90 nm or at least 100 nm or least 110 nm or at least 120 nm.

In some embodiments, the selected phage length value may be greater than 50 nm but less than a wildtype type phage length. For example, the selected phage length value may be greater than 50 nm but less than 880 nm; or at least 55 nm but less than 880 nm or at least 60 nm but less than 880 nm or at least 70 nm but less than 880 nm or at least 80 nm but less than 880 nm or at least 100 nm but less 880 nm or greater than 50 nm but less than 850 nm; or at least 55 nm but less than 850 nm or at least 60 nm but less than 850 nm or at least 70 nm but less than 850 nm or at least 80 nm but less than 850 nm or at least 100 nm but less 850 nm or greater than 50 nm but less than 820 nm; or at least 55 nm but less than 820 nm or at least 60 nm but less than 820 nm or at least 70 nm but less than 820 nm or at least 80 nm but less than 820 nm or at least 100 nm but less 820 nm.

In some embodiments, the selected phage length value may be greater than a wildtype type phage length. For example, the selected phage length value may be greater than 900 nm or at least 920 nm or at least 940 nm or at least 960 nm or at least 980 nm or at 1000 nm.

In some embodiments, the selected phage length may be from 10 nm to 150 nm or from 10 nm to 120 nm or from 10 nm to 100 nm or from 10 nm to 40 nm or from 60 nm to 120 nm. Phage populations having such lengths may be preferred for imaging applications, when phages are used a biological probe.

In some embodiments, the selected phage length value may be from 100 nm to 10 microns or from 100 nm to 5 microns or from 100 nm to 2 microns or from 100 nm to 1 micron or from 100 nm to 800 nm or from 950 nm to 10 microns or from 1 micron to 10 microns. Phage populations having such lengths may be preferred when phages are used in implant applications, such as hydrogel and/or scaffold applications.

The produced homogeneous phage population may have a phage count of at least 1e12 pfu or at least 3e12 pfu or at least 5e12 pfu or at least 1e13 pfu or at least 3e13 pfu or at least pfu or at least 1e14 pfu or at least 3e14 pfu or at least 5e14 pfu or at least 1e15 pfu or at least 3e15 pfu.

The homogeneous phage populations may be used for producing homogeneous, high yield populations of ssDNA packaged inside of phages. The ssDNA may be extracted by lysing the phages. As for a phage length, a length of ssDNA (or a number of bases in it) may be determined by selecting a length (and/or a number of base pairs) of the first artificial plasmid. In general, when all other conditions are the same, a longer (having more base pairs) first artificial plasmid will result in a longer (having more bases) ssDNA, while a shorter (having less base pairs) first artificial plasmid will result in a shorter (having less bases) ssDNA. Due to the homogeneity of the phage populations, the produced ssDNA may also have a high degree of homogeneity, such as homogeneity in size.

The produced ssDNA may contain from 135 to 100,000 bases or from 135 to 80,000 bases or from 135 to 60,000 bases or from 135 to 50,000 bases or from 135 to 40,000 bases or from bases or from 135 to 20,000 bases or from 135 to 15,000 bases or from 135 to 12,000 bases or from 135 to 10,000 bases or any integer number or subrange within these ranges. In some embodiments, the first artificial plasmid may be shorter than a wildtype plasmid. For example, in some embodiments, the produced ssDNA may contain from 179 to 6400 bases or from 135 to 6300 bases or from 135 to 6200 bases or from 135 to 6100 bases or from 135 to 6000 bases or from 200 to 5000 bases or from 200 to 4000 bases or from 200 to 3500 bases or from 200 to 3000 bases or any integer number or subrange within these ranges.

In some embodiments, the first artificial plasmid may be longer than a wildtype plasmid. For example, the first artificial plasmid may contain from 6450 to 100,000 bases or from 6500 to 100000 bases or from 6500 to 80,000 bases or from 6600 to 70,000 bases or from 6800 to bases or from 6800 to 50,000 bases or from 7000 to 40000 bases or from 7000 to 35000 bases or from 7000 to 30000 bases or from 7000 to 20000 bases or from 7000 to 15000 bases or any integer number or subrange within these ranges.

The present method may allow producing homogeneous phage populations with a high phage count without a need for purifying a desired portion of a phage population, i.e. a portion, which has a desired phage length value, from undesired phage portions, i.e. phage portions, which are not substantially close to the desired phage length value. For example, the present method does not include enriching desired portion of a phage population by PEG precipitation and column separation. Nevertheless, in some embodiments, the method may include purification of the produced phage population. For example, the present method may involve purification to remove unwanted and/or contaminating proteins from the phage population. Such purification may be performed, for example, using cesium chloride gradient ultracentrifugation and column separation.

Homogeneous phage populations may be used for a number of applications.

In some embodiments, homogeneous phage populations may be used as a delivery vehicle for delivery an active agent, which may be attached to and/or conjugated with phages of the phage population, to a particular area of a body of a subject, such as a mammal, e.g. a human. The active agent may be, for example, a therapeutic agent and/or an imaging agent Accordingly, the homogeneous phage population may be used in a therapeutic and/or imaging method, which may involve administering the homogeneous phage population to a subject, such as a mammal, e.g. a human being. The homogeneous phage population may be, for example, administered topically, enterally or parenterally. For example, the homogeneous phage population may be swallowed, injected or inhaled.

In some embodiments, the homogeneous phage population may be administered intravascularly. In some embodiments, the homogeneous phage population may be administered intracranially. In some embodiments, the homogeneous phage population may be administered intradermally, subcutaneously or via intramuscular injections. In certain embodiments, the homogeneous phage population may be administered, for example, intravascularly or intracranially, for treating and/or imaging a tumor, such as a central nervous system (CNS) tumor. The homogeneous phage population may be useful for treating both adult and pediatric CNS tumors. CNS tumors include tumors of neuroepithelial tissue, such as astrocytic tumors, oligodendroglial tumors, oligoastrocytic tumors, ependymal tumors, choroid plexus tumors, astroblastoma, neuronal and mixed neuronal-glial tumors, tumors of the pineal region, embryonal tumors; tumors of cranial and paraspinal nerves; tumors of the meninges, such as tumors of meningothelial cells, sesenchymal tumors, primary melanocytic lesions, haemangioblastoma; tumors of the haematopoietic system; germ cell tumors; tumors of the sellar region.

A homogeneous phage population may be a part of a composition, which may be a pharmaceutically acceptable composition. The composition may further include an acceptable carrier, which may be, for example, a sterile buffer, such as PBS buffer or saline buffer, or purified water, such as Mille-Q water. The composition may also include one or more cell media components, such as blood derived serum, and/or one or more components, such as enzymes, gelatin and amino acids.

Figure 12:
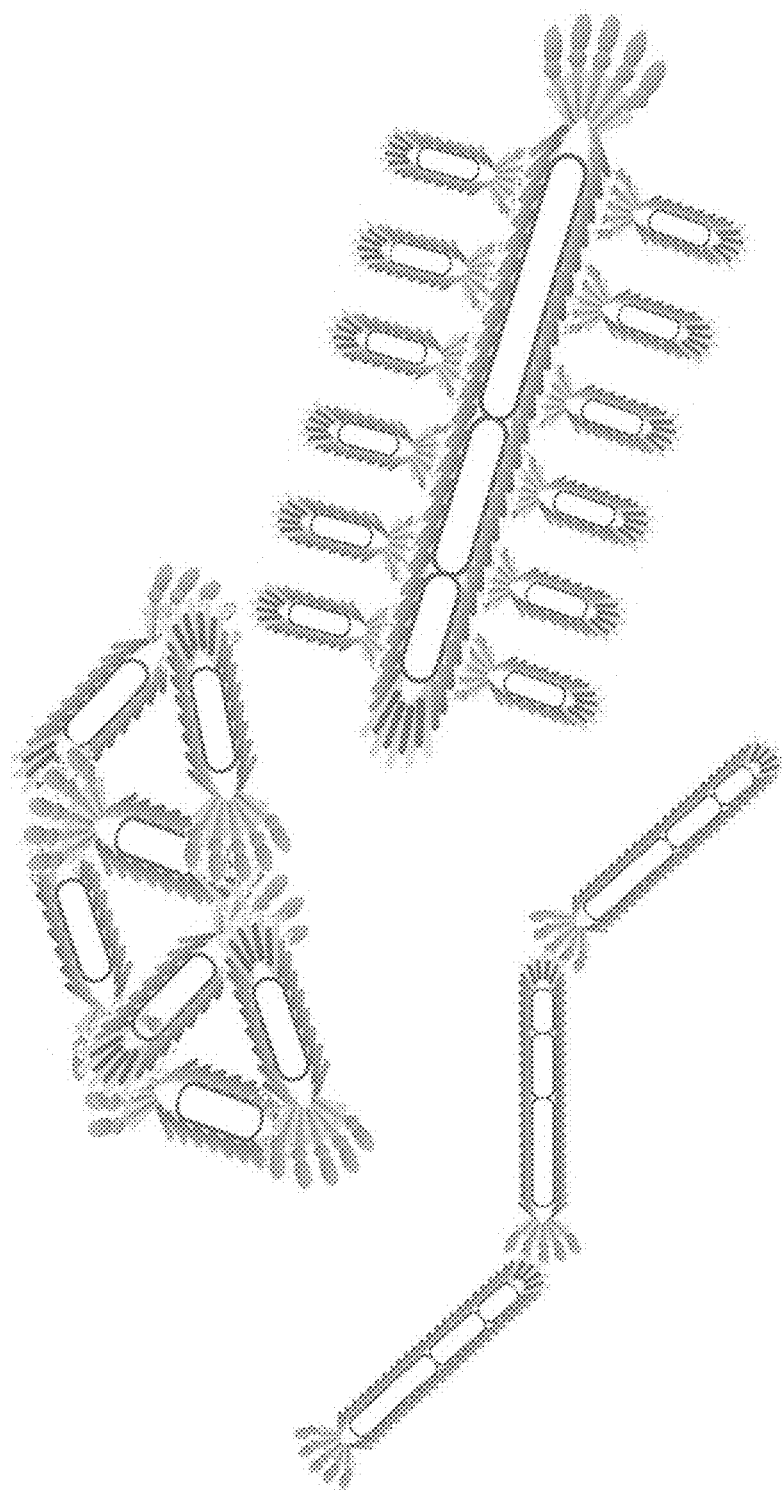
FIG. 12 schematically illustrates multi-phage scaffolds & nanostructures.

A phage concentration in the composition may vary. For example, a phage concentration may be from 1 e10 to 1 e15 pfu/ml or from 1 e11 to 1 e15 pfu/ml or 1 e12 to 1 e15 pfu/ml. In some embodiments, the homogeneous phage population may be implanted in a body of a subject, such as a mammal, e.g. a human. In certain embodiments, the homogeneous phage population may be a part of an implant, which may be, for example, one or more of a scaffold, a hydrogel and a nanostructure. The implant may act as a delivery and/or detector device. Courchesen et al, Advanced Materials, 2014, 26(11), 3398-3404), and Chen et al, Advanced Materials, 2014, 26(30), 5101-5107 demonstrate method of crosslinking phage solutions to create viral scaffolding for various materials. Flynn et al, Acta Materialia, 2003, 51(19), 5867-5880, Huang et al, Nano Lett., 2005, 5(7), 1429-1434, and Hess et al, ACS Synth. Biol., 2013, 2(9), 490-496 demonstrate some methods of assembling phage in structures, such as nanostructures. Implant type viral hydrogels may be produced via a variety of building methods, such as glutaraldehyde crosslinking, layer-by-layer deposition, nanoparticle linkers, covalent bonding, DNA/sortase binding, lyophilization, photodynamic or UV crosslinking. FIG. 12 illustrates, for example, multiphage scaffolds and/or nanostructures.

In some embodiments, an active agent may be an imaging agent. An imaging agent may be an agent that is capable to produce a signal, the detection of which may provide an image of an area of the subject's body, such as a tumor area. For example, an imaging agent may be a fluorescent imaging agent, such as a fluorescent label; a magnetic imaging agent, such as a magnetic nanoparticle; a radioactive imaging agent, such as a radioactive label; an infrared imaging agent; a photoluminescent imaging agent. One example of an imaging agent may be carbon nanostructure, such as a carbon nanotube, which may be for example, a single wall carbon nanotube. Nanostructure imaging agents conjugated to phages are disclosed, for example, in US 20130230464, which is incorporated herein in its entirety.

In some embodiments, a signal from an imaging agent may be used to track and diagnose cells or masses in a body of a subject, such as a human. For example, a signal from an imaging agent may be used to track and diagnose cells or masses in a brain and/or spinal cord of a subject, such as a human. A signal from an imaging agent may be also used to visualize a treatment over time.

In some embodiments, an active agent may be an infrared imaging agent, such as a carbon nanostructure, such as a carbon nanotube, which may be a carbon nanotube, such as a single wall carbon nanotube. In some embodiments, the imaging agent may be an organic or inorganic dye, which may emit in the near infrared range, which may be a range from 700 nm to 2000 nm or from 800 nm to 1900 nm or from 900 nm to 1800 nm or from 800 nm to 1750 nm or from 1100 nm to 1700 nm or value or subrange within these ranges. For example, a dye may be sodium yttrium fluoride doped with ytterbium and erbium. To detect an infrared signal from the infrared imaging agent, after it has been administered to a subject, such as a human, together with the homogeneous phage population, an infrared imaging system disclosed in Ghosh et al, PNAS 2014 111 (38) 13948-13953 may be used. Such system may have imaging depths such as 10 cm.

In some embodiments, an active agent may be a fluorescent imaging agent, such as, for example, Cy5.5 or Alexa-647. In some embodiments, a fluorescent imaging agent may be conjugated directly to a phage coat protein, such as pVI, pVII, pVIII or pIX. Yet in some embodiments, a fluorescent imaging agent may be conjugated to another moiety, which is conjugated directly to or expressed by a coat protein of the phage. For example, a fluorescent imaging agent may be conjugated to chlorotoxin, which is directly conjugated to or expressed by pIII protein of the phage. Imaging using a fluorescent imaging signal may involve detecting a fluorescent signal from the label after it has been administered to a subject, such as a human, together with the homogeneous phage population. For the detection, a multiphoton spectrometer or microscope may be used.

In some embodiments, an active agent may be a therapeutic agent. For example, in some embodiments, a therapeutic agent may be an anticancer agent, such as a chemotherapy agent, e.g. doxorubicin. Use of chemotherapy agents with phages is disclosed, for example, in Ghosh et al, ACS Synth Bio., 2012 1(12), 576-582. In some embodiments, a therapeutic agent may be a small molecule. Non-limiting examples of therapeutic agents include siRNA or small DNA for cell-disruption, adjuvants for immunotherapy, nanoparticles such as gold nanoparticles, or theranostics including photodynamic therapy agents such as IR700. A host of agents may be conjugated to the phage via methods such as EDC chemistry, streptavidin-biotin strategies, zinc-finger sortase strategies, metal chelating linkers such as DOTA-NHSester, thiol alkylation, maleimide modifications, and N-terminal transamination. Other amino acid handles may be used including cysteine residues for di-sulfide bonds and tyrosine residue modifications. Peptide sequences conferring affinity to molecules of interest (as determined by phage display panning) may also be engineered to the coat proteins of the phage. (Bernard et al, Front Microbiol, 2014, 5(734), PMC4274979) (Hess et al, Bioconjug Chem., 2012, 23(7), 1478-1487)

In some embodiments, the homogeneous phage population may be a population of phages conjugated with a targeting moiety. The targeting moiety may be such that it preferentially binds to a particular type of cells compared to other cells. For example, the targeting moiety may be a tumor targeting moiety, i.e. a targeting moiety that binds preferentially to tumor cells compared to other types of cells, e.g. normal cells. In some embodiments, the targeting moiety may be chlorotoxin. Chlorotoxin may selectively and/or preferentially bind to certain types of tumors, such as gliomas and tumors of neuroectrodermal origin such as medulloblastomas, neuroblastomas, melanomas, primitive neuroectodermal tumora (PNETS), and small cell lung carcinoma.

In some embodiments, homogeneous phage populations, with or without an active agent, may be used for treating a plaque caused by or associated with a neurogenerative disease, such as an Alzheimer's disease and other types of dementia; Parkinson's disease (PD) and PD-related disorders; prion disease; motor neurone diseases; Huntington's disease, spinocerebellar ataxia; spinal muscular atrophy.

The present inventors also developed a complex comprising a phage, such as a filamentous phage, and chlorotoxin, which may be conjugated to the phage or expressed by the phage during phage assembly. For example, chlorotoxin may be conjugated to or expressed by the phage's coat protein, such as pIII protein, or expressed by the phage's coat protein, such as pIII protein, during the phage assembly through engineering phage sequence. In some embodiments, the phage may be a wildtype phage. In some embodiments, the phage may be an engineered phage, such as a phage, which is a part of a homogeneous phage population discussed above. In some embodiments, chlorotoxin may be a labeled chlorotoxin, i.e. chlorotoxin with one or more labels attached to and/or conjugated with it. The label may be, for example, a radioactive label or a fluorescent label. One example of example of labeled chlorotoxin may be Cy5.5 labeled chlorotoxin, which is a combination of chlorotoxin and a fluorescent material Cy5.5.

Chlorotoxin-phage may be prepared by incorporating a chlorotoxin encoding sequence, such as SEQ ID No. 1, into one of phage coat protein genes of a plasmid, so that the chlorotoxin will be expressed by the corresponding coat protein. For example, the chlorotoxin encoding sequence may be incorporated into pIII gene of M13 bacteriophage and thus, chlorotoxin may be expressed by pIII protein. A phage for expressing chlorotoxin may be any phage whose genome may be edited. For example, a phage for expressing chlorotoxin may be any of the phages disclosed above. For example, the phage may be one of filamentous or filamentous phages disclosed above. In some embodiments, a phage for expressing chlorotoxin may be T4 phage, T7 phage, tobacco mosaic virus or potato virus.

For the wildtype phage, the chlorotoxin encoding sequence may be incorporated into a phage coat protein gene, such as pIII gene, of a wildtype helper phage to produce a helper phage construct containing the chlorotoxin encoding sequence.

Yet for the engineered phage, the chlorotoxin encoding sequence may be incorporated into a phage coat protein gene, such as pIII gene, of the first or second artificial plasmid discussed above. For example, in some embodiments, for the engineered phage, which is a part of the disclosed above homogeneous phage populations, the chlorotoxin encoding sequence may be incorporated into the modified helper phage plasmid, which acts as the second artificial plasmid, to produce a modified helper phage construct containing the chlorotoxin encoding sequence.

The plasmid containing the chlorotoxin encoding sequence may be transformed through a bacterial strain, such as the ones discussed above. For the wildtype phage, the plasmid containing the chlorotoxin encoding sequence may be transformed by itself without other plasmids. For the engineered phage, the plasmid containing the chlorotoxin encoding sequence may be co-transformed with the other plasmid disclosed above. For example, when the second artificial plasmid contains the chlorotoxin encoding sequence it may be co-transformed with the first artificial plasmid. When the first artificial plasmid contains the chlorotoxin encoding sequence it may be co-transformed with the second artificial plasmid. The products of transformation and or co-transformation may be amplified as discussed above and also in examples below.

In some embodiments, chlorotoxin-phages may be further conjugated with an active agent, which may be an imaging agent and/or a therapeutic agent. For example, when chlorotoxin is expressed by the pIII protein of the phage, an imaging agent, such as a fluorescent label or a carbon nanostructure may be conjugated or attached to the pVIII protein of the phage. For example, a fluorescent label, such as AlexaFlour may be conjugated with the pVIII protein through a reaction with side chains of lysine groups. For attaching a carbon nanostructure, such as a single wall carbon nanotube, DSPH or other carbon nanotube complexing peptide may be conjugated with or expressed by the pVIII protein of the phage. This may be accomplished by incorporating a sequence for DSPH or a sequence for a carbon nanotube complexing peptide at the pVIII gene of a respective helper phage sequence before its transformation into a bacterial strain.

Figure 11:
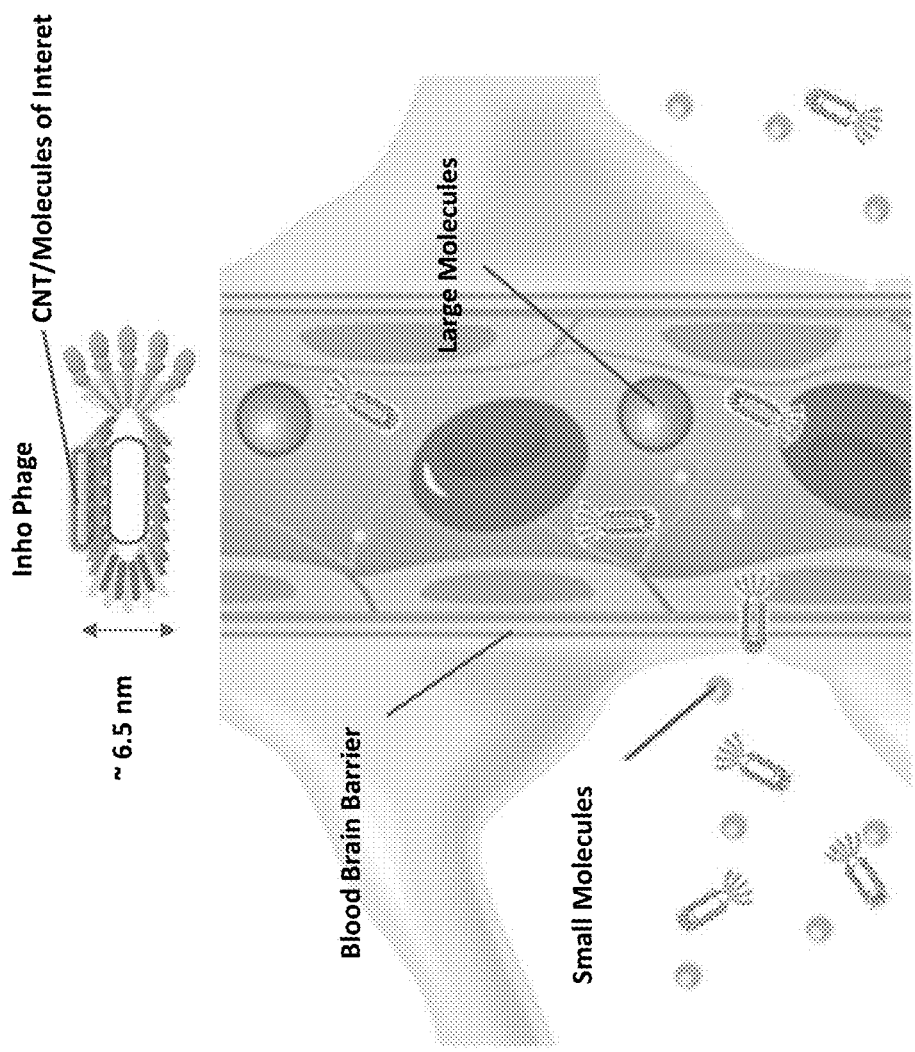
FIG. 11 schematically illustrates passage of small CTX phage across the BBB.

The homogeneous phage populations and/or CTX-phage populations may have an ability to penetrate a blood brain barrier in subject such as a human, see FIG. 11 as well as additional discussion in Example below. For example, phage populations having lengths of no more than 900 nm or no more than 800 nm or no more than 700 nm or no more than 600 nm or no more than 500 nm or nor more than 400 nm or no more than 300 nm or no more than 200 nm or no more than 150 nm or no more than 100 nm may have an ability to penetrate a blood brain barrier when administered intravascularly.

The homogeneous phage populations may be also used in a method of mass producing ssDNA of varying lengths/sequences. For example, homogenous phage populations produced with desired length or sequence of ssDNA packaged within may be produced at titers of at least 1e14 or at least 1e15 or at least 3e15 or at least 1e16 phage from 10 L growths. These phage may be lysed and high yields of ssDNA extracted for use.

The present application also provides a kit for making a homogeneous phage population, which may include the first artificial plasmid disclosed above; and the second artificial plasmid disclosed above. In addition, the kit may include a bacterial strain, which may be used for to con-transforming the first and the second artificial plasmids into it to produce a homogeneous phage population.

Embodiments described herein are further illustrated by, though in no way limited to, the following working examples.

Example

M13 Phage Assembly System for Optimal Blood Trafficking, Tumor Penetration, and Passage Across the Blood Brain Barrier This example relates to the functionality of M13 bacteriophage as an engineerable biomaterial for medical imaging and therapy applications particularly in the case of tumor diagnosis. M13 phages of engineered sizes (less than <50 nm to above a micron in range), termed 'inho' phages were successfully assembled. M13 phages displaying chlorotoxin peptide on the tail capsid of M13 were also successfully assembled. The construction of shorter phage may improve on the extravasation and blood trafficking of M13 probe systems while retaining its multi-functional capsid proteins which may allow simultaneous targeting, detecting, and/or delivery of various agents, such as active agent, e.g. a therapeutic agent and/or an imaging agent, to a desired body part, such as a cancerous tissue or a diseased tissue. Construction of phage expressing chlorotoxin (CTX) as well as its reduced size may allow for the passage of M13 probe systems across the blood-brain barrier (BBB) and the potential targeting to adult and pediatric brain tumors.

Technical Description

M13 filamentous bacteriophage is composed of a circular single stranded DNA (ssDNA) encapsulated by the major coat protein p8 and minor cap proteins p3, p6, p7, p9 [1, see section "References" below]. These proteins can be engineered to display or attach various targeting sequences and nanoparticles or drug molecules—effectively creating a phage shuttle that carry imaging or therapy agents to specifically targeted cancer cells [2]. In our system, we can control the length (or the number of p8 coat) of the M13 phage by manipulating the length of the circular ssDNA plasmid packaged during the M13 assembly process. A set of plasmids (termed "inho") that generate package-able viral genomes with desired sizes (i.e. 100s to 1000s base-pairs), which may be much smaller than the 6407 nucleotides observed in wildtype M13 (~880 nm in length), was created. These package-able genomes may be of varying lengths and contain the phage packaging signal and the f1 origin and termination of replication but none of the phage protein genes. In effect, construct with the inserts produces ssDNA of a given length that signal to be packaged (FIG. 1). To produce minimally sized ssDNA, the packaging signal region may also be removed and the packaging genome retaining the f1 origin may be enough to begin assembly.

Figure 2:
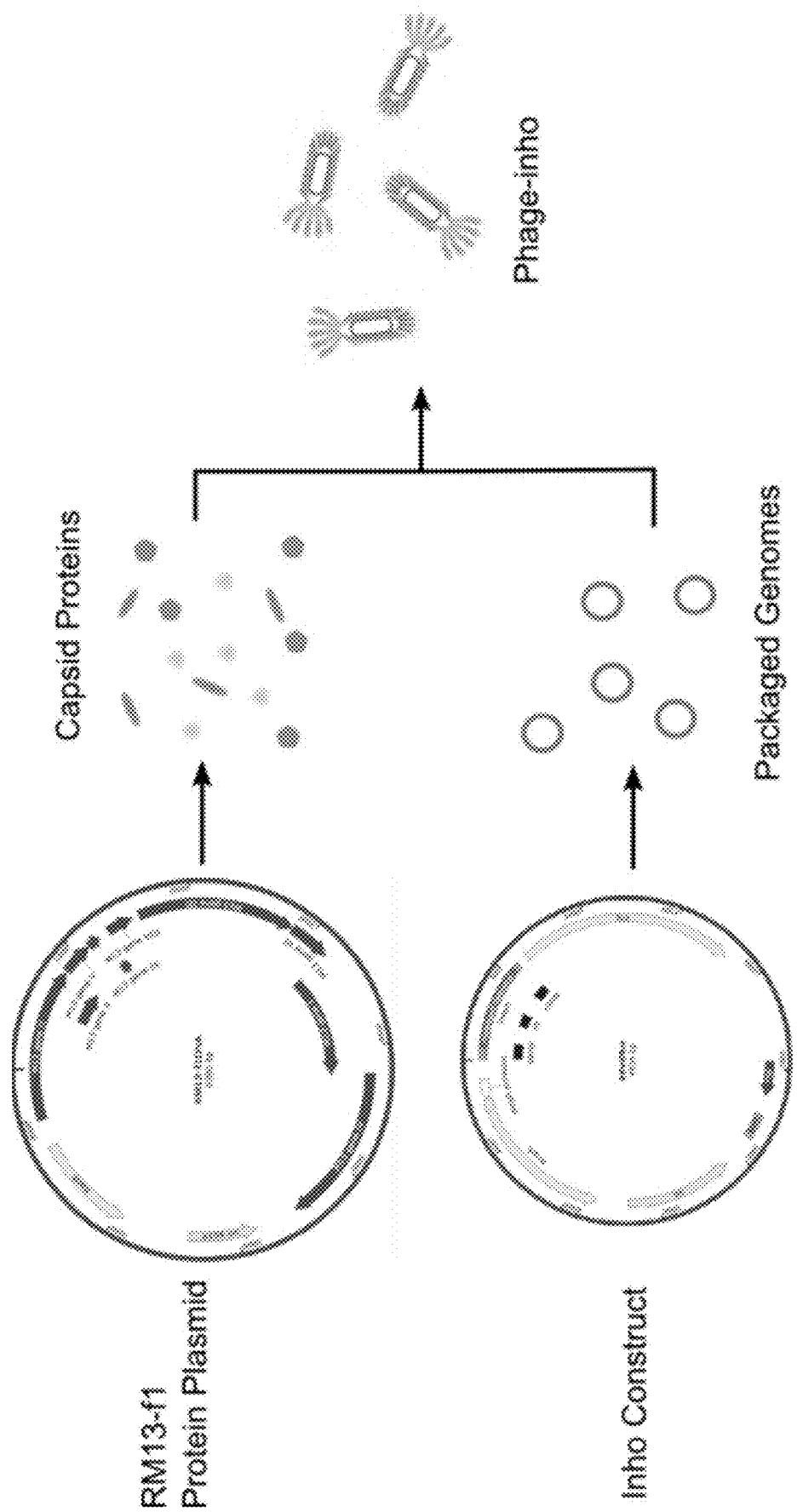
FIG. 2 schematically illustrates phage-inho production: inho plasmids when co-transformed with another plasmid (RM13-f1) coding for phage proteins produce short phage that packages the inho genomes, which control the length of the phage.

In the absence of M13 protein coding in the packaged genomes, a second plasmid (RM13-f1) which expresses all essential phage assembly components but itself lacks the packaging signal and f1 replication origin, was constructed. Only in the presence of both of these two plasmids is phage production of the given size observed (FIG. 2), where inho plasmids are packaged by the proteins translated from the unpackaged large RM13-f1 plasmid.

Co-transformation of an inho and the protein construct into a competent bacterial strain (in the present case XL-1 or DH5a) and overnight amplification of the co-transformed colony provide sufficient number of phage for analysis. Using these two plasmids in concert, one can then proceed to purification of the extruded phage-inhos for biomedical applications. In example, inho1960, inho475, and inho285 with RM13-f1 gives us phage of 280 nm, 100 nm, and 50 nm in length (FIG. 3). Additionally, the RM13-f1 plasmid is open to any manipulations, such as the addition of chlorotoxin display that may further improve on the specificity of phage delivery of an active agent, such as an imaging agent and/or a therapeutic agent.

Chlorotoxin (CTX) is a 36 amino-acid (3995.8 Da) peptide derived from the venom of the *Leiurus quinquestriatus* scorpion. Recent studies have shown that the CTX peptide selectively binds to and invades malignant gliomas (GBM) and tumors of neuroectrodermal origin such as medulloblastomas, neuroblastomas, melanomas, PNETS, and small cell lung carcinoma [3]. Additionally, native CTX as well as fluorophore conjugated CTX tumor paint display the ability to cross the blood-brain barrier (BBB) in both animals and humans with brain tumors, which may make it an ideal trafficking peptide for nanoprobes designed for brain tumor diagnosis and theragnosis. In order to harness these unique properties to the M13 probe system, a phage clone that encodes for CTX on the p3 capping protein of the M13 phage (both wildtype and inho or short phage) was developed. The 36 amino acid sequence of the CTX peptide is incorporated into the gene for p3 as illustrated in FIG. 4.

Figure 5:
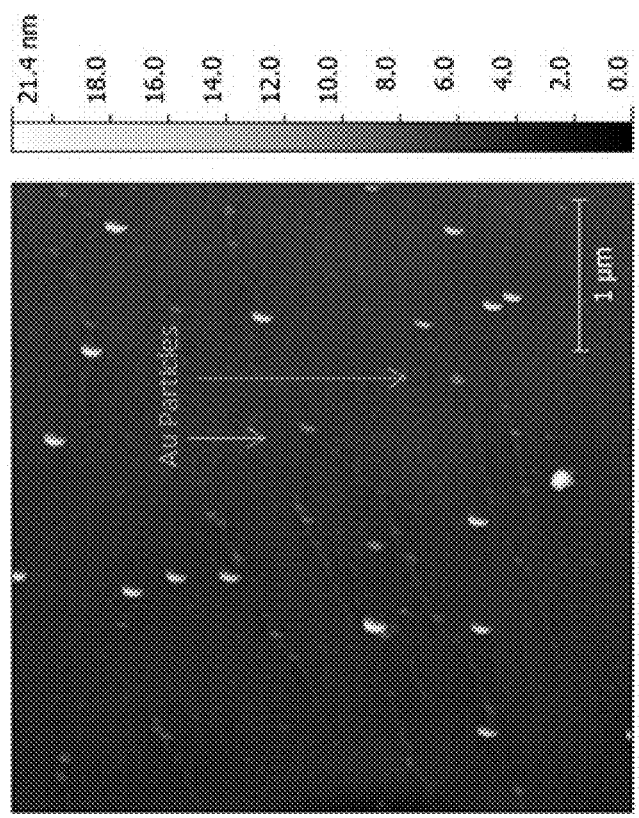
FIG. 5 shows an AFM image of chlorotoxin-phage with negatively charged gold particle interaction at p3.

The CTX peptide is highly positive in charge, an attribute which may be part of the reason for its ability to cross the BBB and target to tumor areas with extracellular matrix which is particularly negative in charge [3]. When suspended with negatively charged citrate stabilized gold/Au nanoparticles, CTX phage electrostatically interacts with the nanoparticles at its CTX-p3 end (FIG. 5).

Figure 6A:
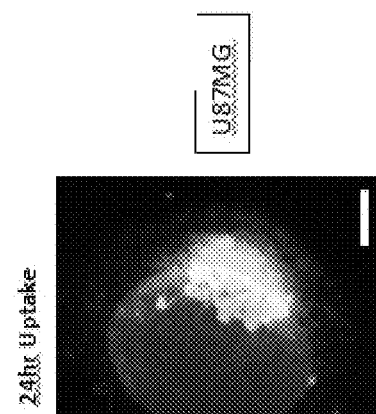
FIG. 6A-D show fluorescent images for internalization of CTX Phage in Adult Human U87MG Glioblastoma and Pediatric Human D458 Medulloblastoma Cells. In vitro cellular uptake and colocalization of CTX phage (red) in the Golgi apparatus (green) in (A & B) human U87MG glioblastoma and (C & D) human D458 medulloblastoma cells. Nuclei shown in blue. (scale bar=5 μm).
Figure 6B:
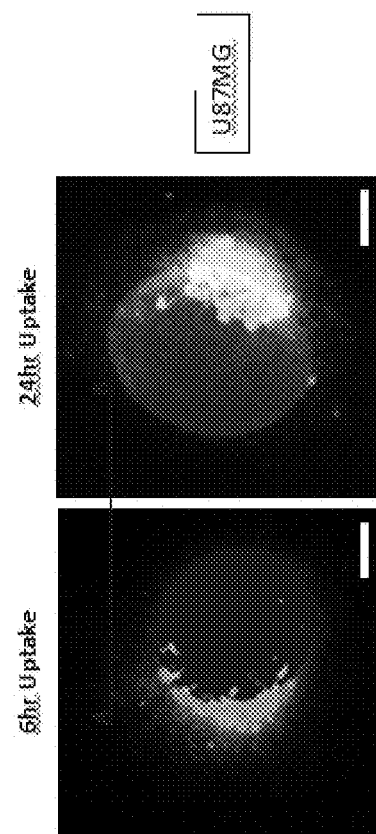
Figure 6C:
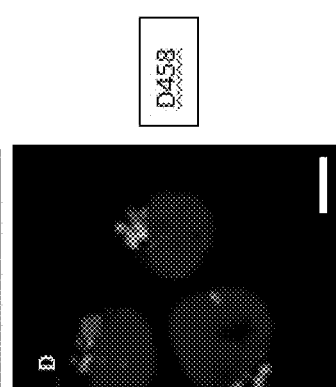
Figure 6D:
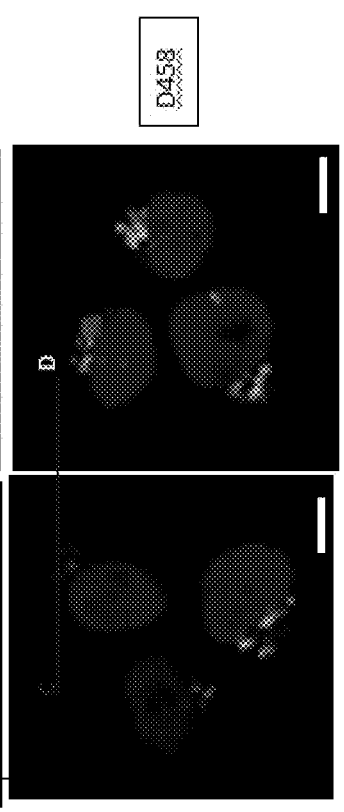

Chlorotoxin also has a distinct in vitro cellular localization and uptake pattern in human glioma versus normal cells, where it localizes near the golgi apparatus in glioma cells. Using the CTX phage particles, in vitro cellular uptake and colocalization of phage particles to the Golgi apparatus in human adult U87MG glioma cells (FIGS. 6A & B) as well as human pediatric D458 medulloblastoma cells (FIGS. 6C & D) as early as 6 hrs following incubation of cells CTX phage with continued accumulation at 24 hrs, were shown, demonstrating the versatility of the CTX phage to target multiple types of brain tumors.

Figure 7:
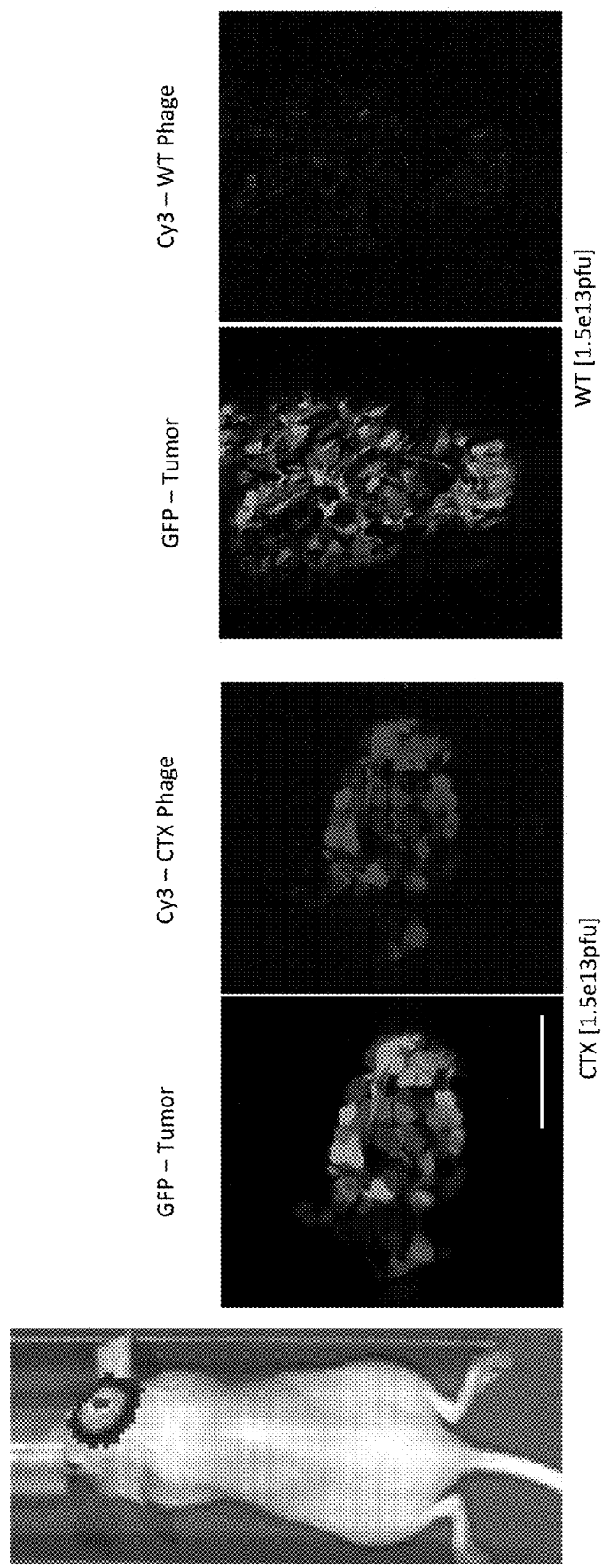
FIG. 7 presents results of Intravital Multiphoton Imaging Showing Tumor Uptake of CTX-Phage in the Brain of a NCR Nude Mice with an Orthotopic Human U87MG Glioma Xenograft.
Figure 8:
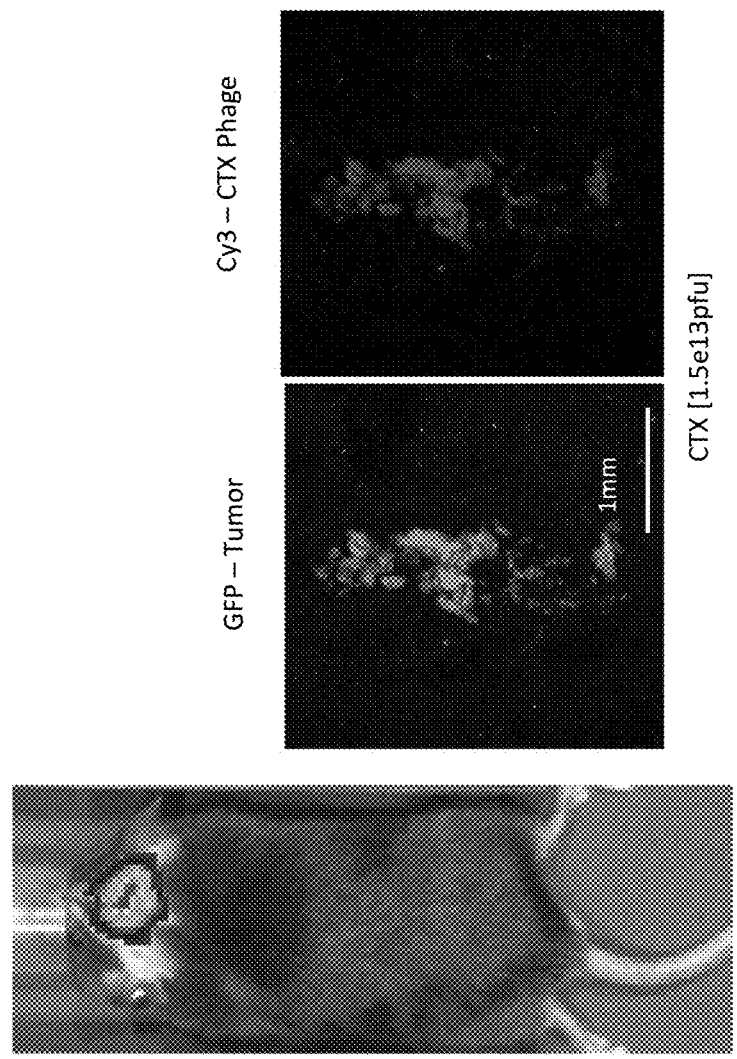
FIG. 8 presents results of Intravital Multiphoton Imaging Showing Tumor Uptake of CTX Phage in the Brain of a C57/BL6 Mouse With an Orthotopic Synergic Mouse GL261 Glioma Xenograft.
Figure 10:
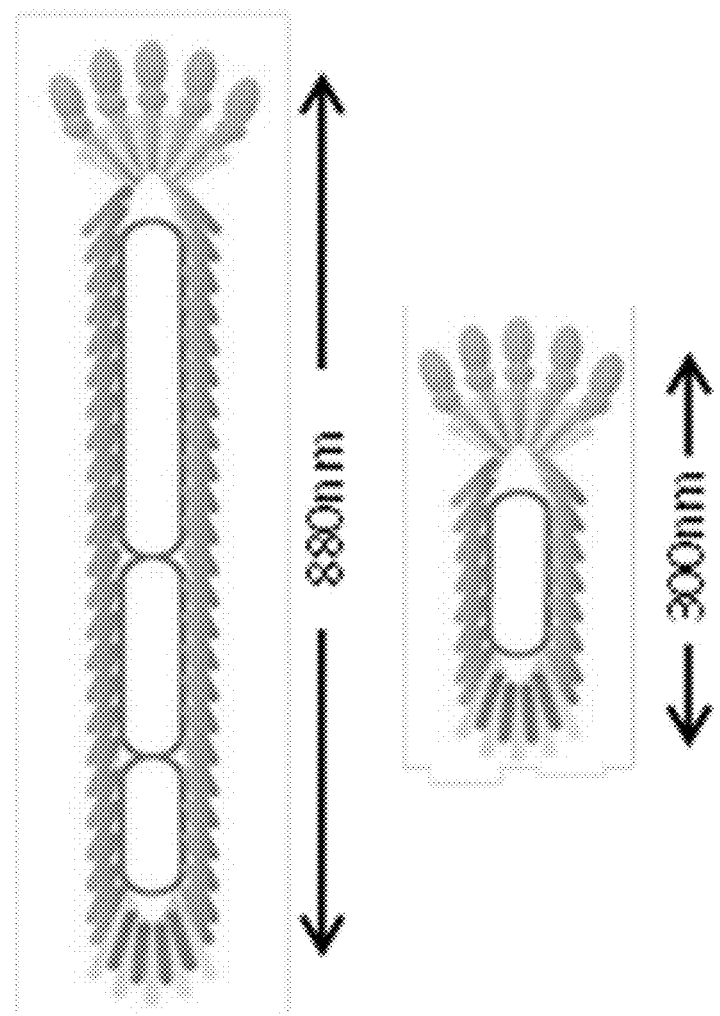
FIG. 10 schematically illustrates small phage model.

In both immunocompromised (FIG. 7) and immunocompetent (FIG. 8) intracranial orthotopic mouse models of GBM, targeting to the tumor site by CTX phage delivered intravascularly via tail vein injection was observed. Accumulation of CTX phage on the tumor surface is observable on a level much greater than wild-type control phage as demonstrated in FIGS. 7 and 8.

It had been previously demonstrated that the M13 bacteriophage can be used as a molecular shuttle for the delivery of various therapy molecules and imaging agents (i.e. single walled nanotubes, SWNT) to the site of tumors. These molecular carriers have been most effective in combination with the second window near infrared (NIRII) imaging system which allows for deep signal penetration through tissue using non-radioactive, inexpensive imaging machinery, see e.g. US 20170017069, Ghosh et al, PNAS 2014 111 (38) 13948-13953. Illustrated here (FIG. 9) is the NIRII brain tumor signals from the dual phage SWNT probe and NIR imaging system which may give surgeons the information needed to remove tumors at the sub-millimeter size level—and those tumors that were not detectable by the naked eye. These preliminary data may reveal successful localization to glioma masses from long SWNT complexed CTX phage (880 nm) as well as short SWNT complexed CTX phage (300 nm).

Advantages and Improvements Over Existing Methods

Firstly, filamentous phages of shorter lengths by constructing a set of small viral ssDNA that are packaged by M13 capsid proteins (these smaller phage retains the M13 major and minor coat proteins) were engineered. Now with the ability to control the aspect ratio of these rigid, rod-like phages one can further improve on M13 based cancer/disease detection or panning by optimizing for phage blood circulation and tumor extravasation. Secondly, collection by cloning for chlorotoxin display on the tail p3 capsid protein of M13 has been added. CTX may induce passage across the BBB and target glioma tumors in vivo. Expression of CTX on M13 may allow capitalizing on its strong affinity for tumors of neuroectodermal origin, increasing its usage for the detection and delivery of novel therapies to treat adult and pediatric brain tumors with the potential to expand the platform for use in other diseases of the central nervous system.

Two Plasmid Phage Assembly Method

Figure 22:
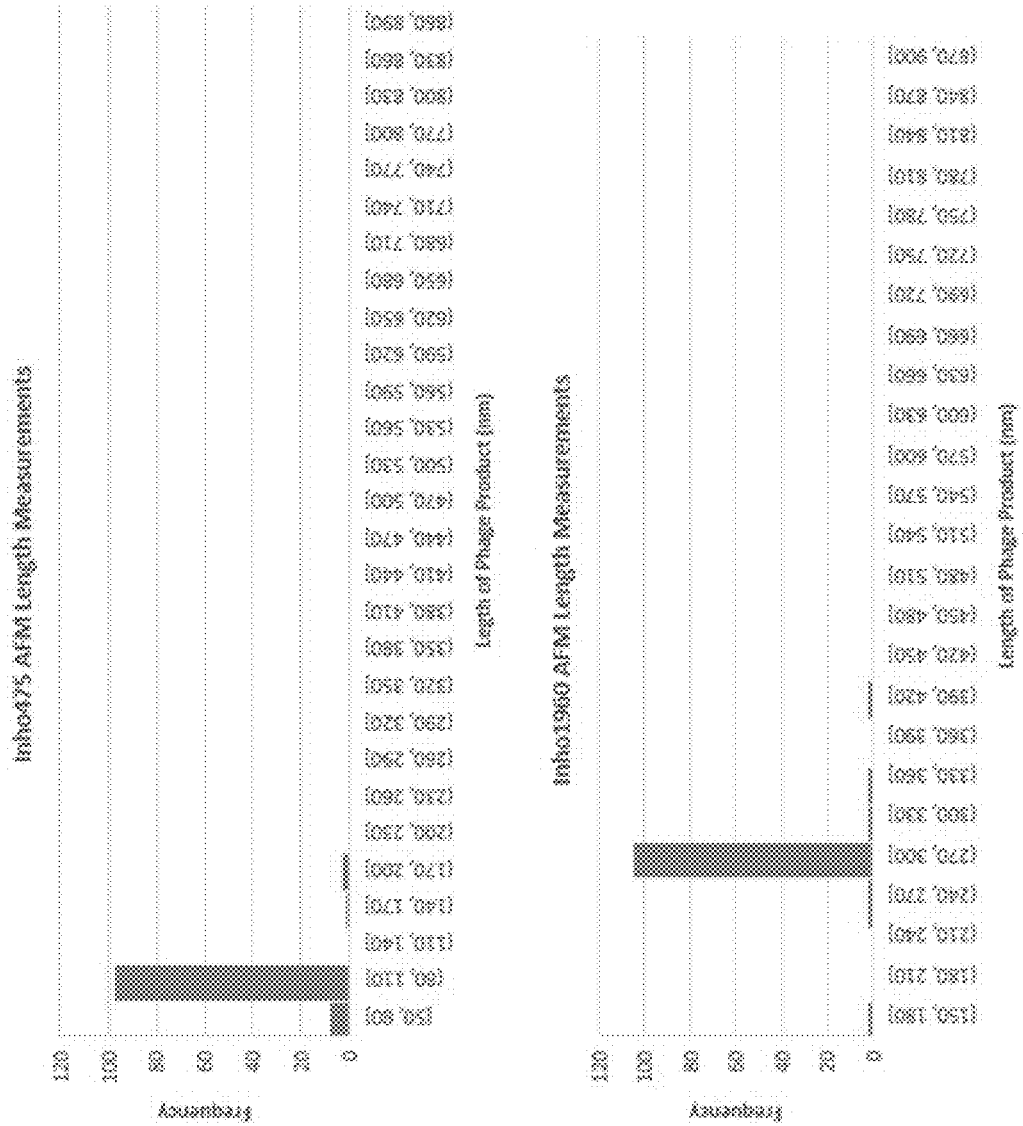
FIG. 22 shows a histogram distribution of inho phage sizes as measured from AFM imaging: for inho475 and inho1960 phages, about 90% of all measured lengths fall within the base size bin.

Preceding work by Specthrie et al. created a plasmid that generates a minimal packaging genome and produced a mixed population of full length phage and smaller phage that are 50 nm in length (though only 1-3% by mass of total population) [4, 5, 6]. The present work differs from Specthrie et al. in two ways. The first is to construct a set of plasmids that generate package-able genomes with any needed size. The second is to generate populations of a shorter size by removing the helper phage using a plasmid that contains all phage proteins but is unable to package its DNA. In this way, homogenous batches of phage with lengths below 50 nm and above (length ranges in the microns also possible) can be produced. FIG. 22 provides evidence of a high degree of homogeneity in length for inho phages. In particular, FIG. 22 presents a histogram distribution of inho phage sizes as measured from AFM imaging: for inho475 and inho1960 phages, about 90% of all measured lengths fall within the base size bin Tumor or Disease Targeting In Vivo The Biomolecular Materials Lab (Belcher Group) at the Koch Institute at MIT has previously demonstrated that targeted M13 bacteriophage conjugated with fluorescent materials may be used to perform in vivo molecular imaging of tumors [1]. However, this method may be limited by inefficient extravasation of the probe into vasculature due to the length of the phage (880 nm). To improve tumor penetration of phage, a system to control and shorten the length of phage while maintaining its multi-functional capsid has been engineered. The geometry and size may play a significant role in the transport, bio-distribution, and internalization of nanoparticles [7, 8]. Upon systemic injection, nanoparticles must: 1) Evade uptake by circulating immune macrophages; 2) Achieve marginalization and escape the circulation to reach blood vessel walls; 3) Extravasate into the tumor interstitium; and finally, 4) bind to or be internalized by cancer cells [9]. Though spherical particles have been the norm in nanomedicine research, non-spherical nanoparticles (i.e. rods, chains, ellipsoids) may be more effective in these areas [10]. Not only are chain or rod-like structures more likely to avoid internalization by macrophages, their shape subjects them to certain torque and tumbling motion that increases contact with the vessel walls. Furthermore, oblong shaped particles are more likely to form multivalent occurances essential for targeting—in the case of the filamentous bacteriophage, avidity of binding can be highly enhanced by the display of materials on all 2700 copies of the body p8 protein. On the other hand, size considerations must be made to accommodate for the high interstitial flow pressure typical of tumor masses. Due to the increased leakiness of tumor vessels and reduced lymphatic drainage, extravasation and delivery of nanoparticles to tumor tissues can be achieved via enhanced permeation and retention (EPR) effects, which is typically seen with smaller particles <100 nm in diameter.

Delivery Past the Blood Brain Barrier

The permeability of the BBB to nanoparticles is affected by a number of factors including size, charge, and surface chemistry of the particles. M13 bacteriophage has been postulated to be able to cross the BBB. While long in length, the structure of M13 is extremely narrow in diameter (~5-6 nm) and easily falls under the hydrodynamic size limit of particles that freely pass the BBB [3, 11]. Engineering the M13 platform to enable easy passage across the BBB may be particularly advantageous in concert with deep tissue imaging technologies. The brain is an organ which is especially difficult to image in depth-imaging the CTX-phage probes may be performed using the near infrared imaging system which has depths up to Ghosh et al, PNAS 2014 111 (38) 13948-1395; Dang et al, PNAS, 2016, 113(19), 5179-5184.

Given the capabilities of the CTX phage to cross across the BBB and internalize to tumor cells, one may utilize the system for simultaneous delivery of imaging agent and gene or chemo-therapies. Combining the inho and CTX designs may allow one to further achieve penetration into tumors, such as glioma and medulloblastoma tumors. Small sizes achievable by inho phage (less than <50 nm) may allow penetration of inho phage across intact/heathy BBB of non-tumor bearing mice. Additionally, due to the high pay load possible with each inho shuttle vs. single molecules such as tumor paint, the M13 shuttles may be particularly important as a means of increasing distribution of drugs past the BBB and for reducing nonspecific systemic effects. Furthermore, the multifunctional M13 shuttle may play a significant role in the imaging detection, drug treatment, and surgical removal of brain tumors which require extremely precise handling for patient safety.

In addition, M13 phage has been studied as a means of reversing the formation of plaques derived from amyloid-like structures in the brain related to Alzheimer, Parkinson and other neurodegenerative diseases [12]. The P3 capsid protein was identified as a major agent with curative potential and was engineered as a recombinant bivalent G3P molecule called General Amyloid Interactive Motif (GAIM) by NeuroPhage Pharmaceuticals or more recently renamed Proclara BioSciences [13]. This small motif was mainly developed in order to overcome the hurdle of delivering M13 bacteriophage across the BBB while retaining the ability of the bacteriophage to bind to beta amyloid protein in the brain. The effectiveness of M13 phage to clear amyloid plaques is not completely captured with GAIM, which suggests that CTX phage as well as inho-phage may be a more powerful alternative to targeting plaques in the brain.

Experimental

Cloning CTX-phage. Helper phage template M13KE was used as the basis of the addition of CTX peptide display at the c-terminal end of the p3 capsid protein (see FIG. 4 for insertion sequence).

Construct Production Steps: Display of CTX insert was achieved through restriction enzyme sites at the p3 region of the New England Biolabs (NEB) M13KE vector. The 108 base-pair CTX insertion and oligos designed with Acc65I and EagI enzyme cut sites were purchased through IDT. The CTX template was used in a PCR reaction (KAPA HiFi Kit) to amplify CTX inserts with the previously mentioned enzyme cut sites and purified through a 1.2% agarose gel run and extraction (QIAquick Gel Extraction). Both the host vector M13KE and the CTX PCR product were digested overnight at 37° C. with Acc65I and EagI NEB enzymes in Buffer 3.1. Dephosphorylation of the host vector post digestion was conducted at 37° C. for 1 hour with 2.54, of rSAP enzyme to reduce recircularization events in the host vector. The final CTX and M13KE digestion products were further purified through agarose gel run and extraction. T4 ligation with the prepped CTX insert and M13KE vector was performed overnight at 16° C.

Figure 13:
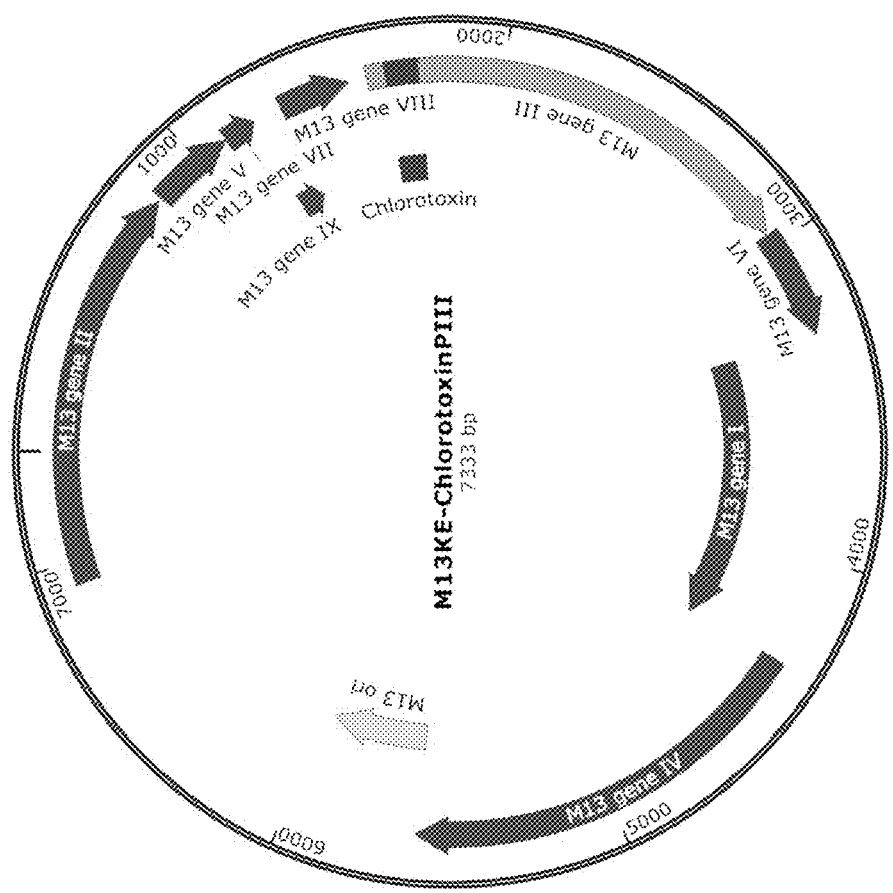
FIG. 13 is a map of CTX insertion.

1-2 µL of the ligation products were transformed according to manufacturer's instructions for competent cells (i.e. XL-1 Blue), prepared in 3 ml of agar top and 1004, of overnight bacterial culture (XL-1 Blue), and incubated on IPTG-X-Gal agar plates overnight at 37° C. Phage plaques from the plates were picked, grown overnight, and prepped for sequencing (QIAprep). Finally, full sequencing of the purified plasmids were verified for desired final M13KE-CTX construct. A map of CTX insertion is shown in FIG. 13.

Cloning RM-13-f1 Constructs. Commercially available helper phage templates M13KE, M13K07, and R408 were used to create RM13-f1 constructs where the intergenic region is reassembled to disrupt the origin for packageable ssDNA replication (f1 site in particular was removed, FIG. 14 presents a part of the removed sequence). Kanamycin resistance site was added to the constructs for identification purposes and ColE1 (p15a-ori) plasmid replication site is included to achieve optimal copy numbers during E. coli growth. Additional functionalization (i.e. CTX on p3, DSPH or CNT complexing peptide display on p8, HIS-tag on p3, separation of overlapping capsid sequences) of the phage is easily also achieved as described below.

Figure 15:
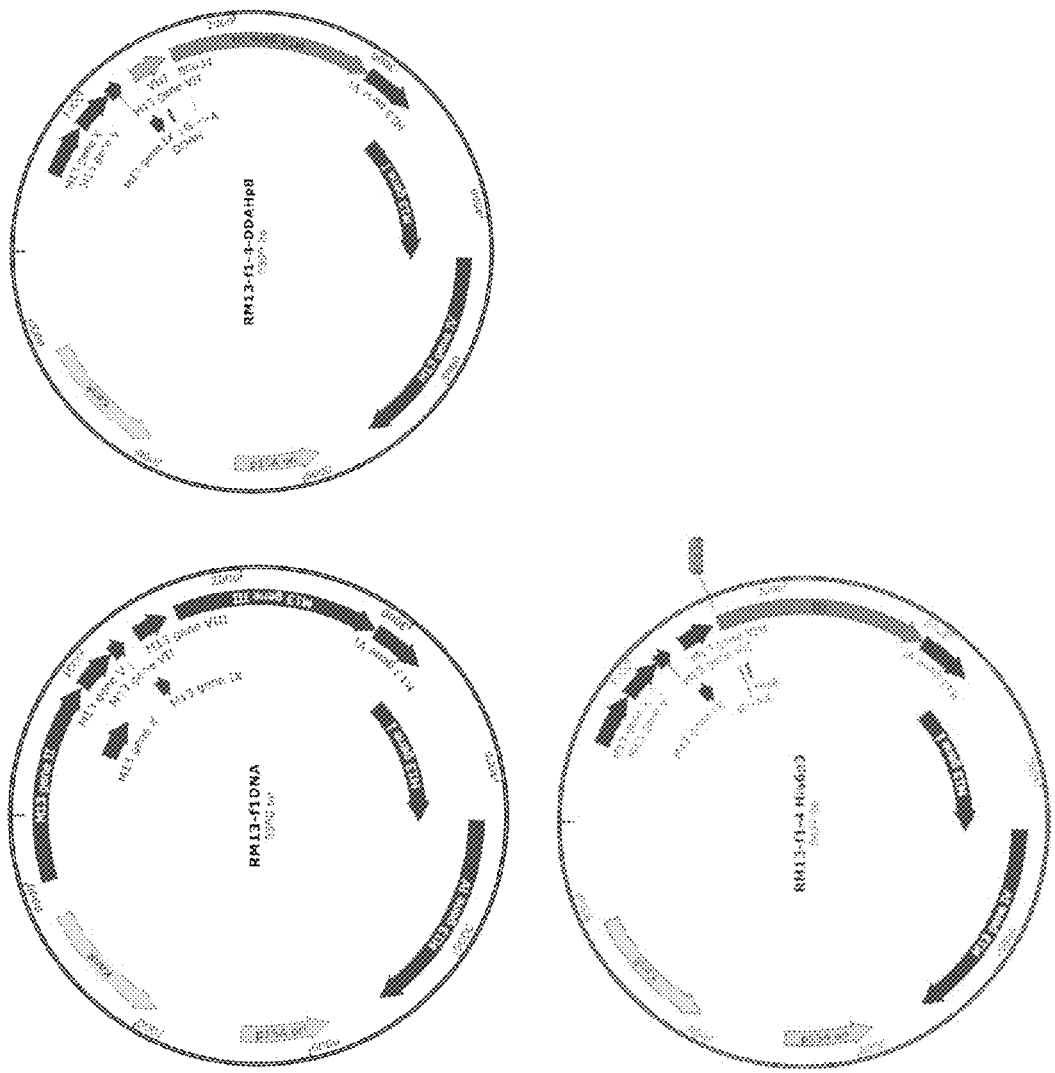
FIG. 15 is a map of RM13-f1, RM13-f1 with p8 modification (DDAH), with p3 modification (HIS6 (SEQ ID NO: 7)), with p8 and p3 modification (DSPH & CTX).

Construct Production Steps: Plasmid cloning by PCR with restriction enzyme or gibson master assembly techniques were used to create constructs from vector fragments of interest or to add insertions important to functionalizing the capsid proteins. All oligos and small DNA inserts were purchased through IDT. PCR reactions were performed (KAPA HiFi Kit) to amplify inserts and vectors with/out the enzyme cut sites or gibson overlapping overhangs. PCR products were purified through a 1.2% agarose gel run and extraction (QIAquick Gel Extraction) or DNA spin columns. Standard ligation or Gibson reactions were conducted as appropriate. 1-2 µL of the ligation or Gibson products were transformed according to manufacturer's instructions for competent cells (i.e. XL-1, DH5alpha) and incubated on antibiotic kanamycin agar plates overnight at 37° C. Bacterial colonies from the kanamycin plates were picked, grown overnight, and prepped for sequencing (QIAprep). Finally, full sequencing of the purified plasmids were verified for desired final RM13-f1 construct. FIG. 15 is a map of RM13-f1, RM13-f1 with p8 modification (DDAH), with p3 modification (HIS6 (SEQ ID NO: 7)), with p8 and p3 modification (DSPH & CTX).

Figure 17:
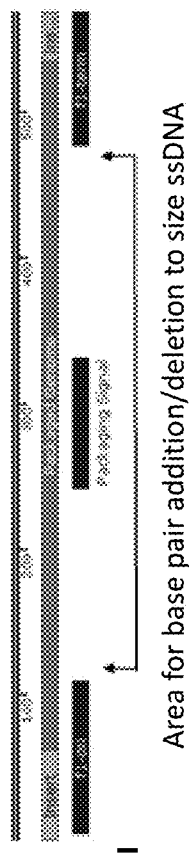
FIG. 17 schematically depicts ssDNA sequence site of inho construct.

Cloning Inho Constructs. Inho construct were assembled via the incorporation of the f-1 origin of replication (modified for origin of ssDNA replication only), f-1 termination site (a repeat of the f-1 origin with deletions that render ineffective the nicking of the plasmid for ssDNA production), and the packaging signal (PS). Ampicillin resistance site was added to the constructs for identification purposes and ColE1 plasmid replication site is included to achieve optimal copy numbers during E. coli growth. Addition and deletion of base-pairs in the ssDNA region (as demonstrated in the case of inho1960, inho475 etc) may be easily achieved via the cloning procedures described. FIG. 16 shows sequences of f1 replication modified for origin only (SEQ ID No. 3), termination only (SEQ ID No. 4 and SEQ ID No. 5), and the packaging signal as found in M13-ori (SEQ ID No. 6), while FIG. 17 identifies sections of ssDNA, which may be manipulated by for example, adding and/or replacing and/or deleting bases therein.

Figure 18:
FIG. 18 schematically illustrates examples of inho sequence insertions for modified ssDNA length.
Figure 19:
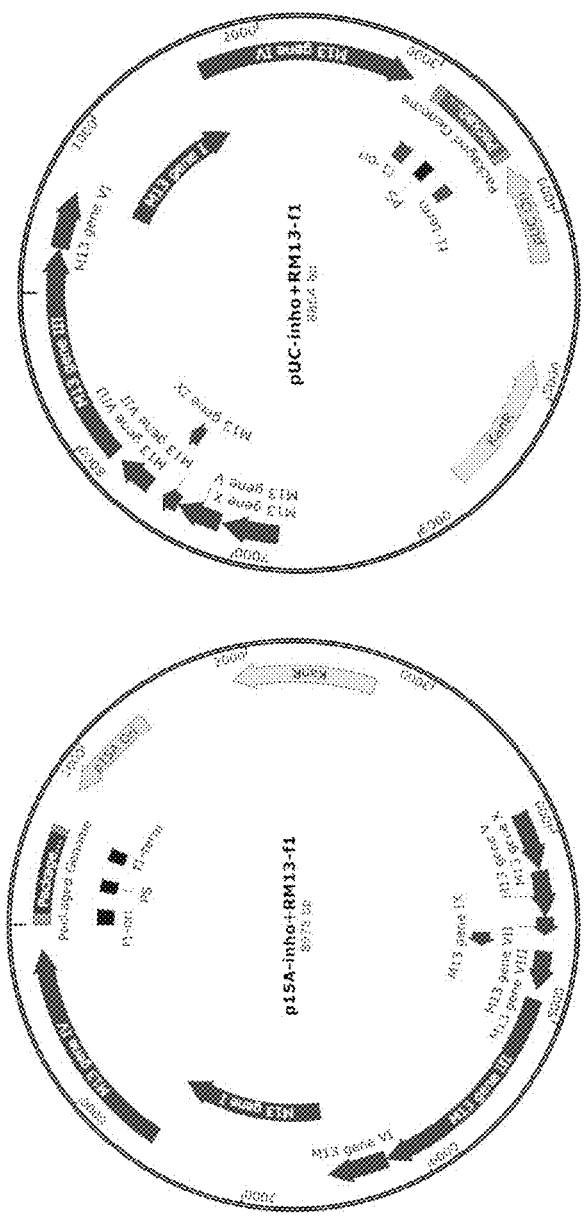
FIG. 19 schematically illustrates examples of inho ssDNA production sequence combined with RM13-f1 protein sequences: with differing plasmid replication origins (p15Ori and pUC Ori) for varying yield effects during *E. coli* growth.

Construct Production Steps: Plasmid cloning by PCR with restriction enzyme or gibson master assembly techniques were used to create constructs from fragments of interest or to add insertions important to ssDNA packaging and to change the length of the inho-phage. Insertions such as EGFP and GLuc sequences were used to test the efficacy of inho constructs with different ssDNA production region (See FIG. 18). All oligos and small DNA inserts were purchased through IDT. PCR reactions were performed (KAPA HiFi Kit) to amplify inserts and vectors with/out the enzyme cut sites or gibson overlapping overhangs. PCR products were purified through a 1.2% agarose gel run and extraction (QIAquick Gel Extraction) or DNA spin columns.

Standard ligation or Gibson reactions with inserts or fragments were conducted as appropriate. 1-2 µL of the ligation or Gibson products were transformed according to manufacturer's instructions for competent cells and incubated on ampicillin agar plates overnight at 37° C. Bacterial colonies from the ampicillin plates were picked, grown overnight, and prepped for sequencing. Full sequencing of the purified plasmids were verified for desired final inho construct.

Amplifying Inho-Phage

Phage Plates: 50 ng each of inho construct of desired base pair length and RM13-f1 with desired capsid proteins, such as e.g. CTX and/or DSPH, sequences are co-transformed through heat shock in tetracycline resistant bacterial strain (i.e. XL-1 Blue) and grown SOC Media. The SOC growth is spread over kanamycin+ampicillin agar plates and incubated overnight at 37° C. Resulting bacterial colonies are stored up to 3 months for amplification of phage.

Amplification:

1. Sterile LB Media is prepared with tetracycline, kanamycin, and ampicillin at working concentrations of 10 µg/mL, 50 µg/mL, and 100 µg/mL respectively.

2. Bacterial colony picked from plate is grown overnight in LB at 37° C. and 225 rpm.

3. Resulting bacterial culture is spun for 30 min at 8000 rpm to remove E. coli bacteria.

4. The supernatant containing the phage product is stored overnight at 4° C. with 10% PEG/NaCl to precipitate out the inho-phage particles.

5. The phage media is centrifuged again for 40 min at 8000 rpm to pellet out the phage.

6. Resuspend the pellet in sterile buffer or milliQ water.

Figure 20:
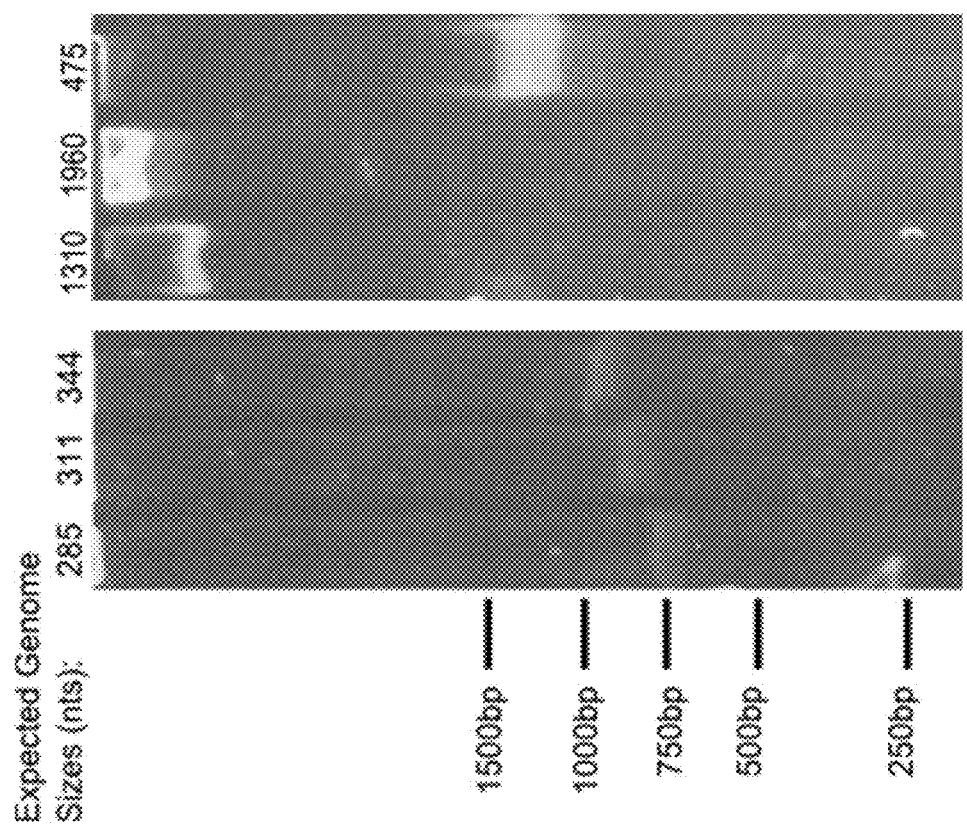
FIG. 20 presents results of analysis of packaged genomes: TBE-PAGE gel of the inho 285, 311, 344, 475, 1310, 1960 constructs, stained with SYBR-Gold. Inho ssDNA run higher than the reference ruler (designed for dsDNA).
Figure 21:
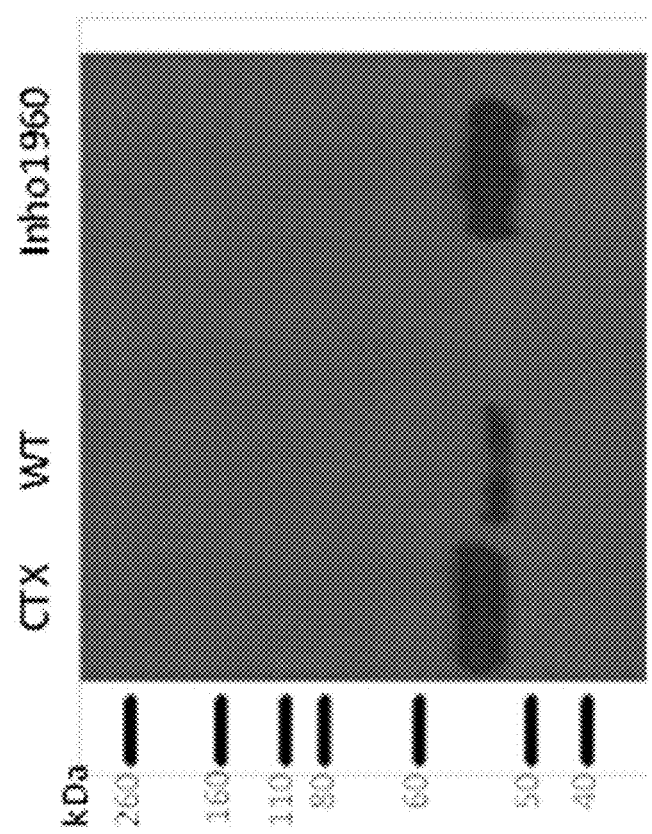
FIG. 21 presents results of analysis of p3 coat protein: anti-p3 Western Blot from NU-PAGE gel run of inho, CTX, and Wildtype phage.

Confirming Phage Identity:
1. Samples of the resuspend phage were denatured by heat and SDS and run on TBE gels to identify the packaged ssDNA (See FIG. 20)
2. Samples of the resuspended phage were denatured by heat and SDS and run on Nu-PAGE gels to check for the presence of p3 capsid protein via Western Blot (See FIG. 21).
3. Diluted samples of phage were imaged via AFM and TEM.

Amplifying CTX-Phage
Phage Plates:
50 ng of the CTX construct was transformed according to manufacturer's instructions for tetracycline resistant, competent cells (i.e. XL-1 Blue), prepared in 3 ml of agar top and 1004, of overnight bacterial culture (XL-1 Blue), and incubated on IPTG-X-Gal agar plates overnight at 37° C. Resulting phage plaques are stored up to 3 months for amplification of phage.

Amplification:
1. Sterile LB Media is prepared with tetracycline at working concentrations of 10 µg/mL.
2. Phage plaque picked from plate is grown overnight in LB at 37° C. and 225 rpm.
3. Resulting bacterial culture is spun for 30 min at 8000 rpm to remove E. coli bacteria.
4. The supernatant containing the phage product is stored overnight at 4° C. with 2.5% PEG/NaCl to precipitate out the inho-phage particles.
5. The phage media is centrifuged again for 40 min at 8000 rpm to pellet out the phage.
6. Resuspend the pellet in sterile buffer or milliQ water.

Confirming Phage Production:
1. Samples of the resuspended phage were denatured by heat and SDS and run on Nu-PAGE gels to check for the presence of p3 capsid protein via Western Blot.
2. Diluted samples of phage were imaged via AFM and TEM.

Phage Purification Options:
1. Repeat PEG/NaCl precipitation.
2. Digest with DNase I to reduce DNA debris.
3. Run dialysis against buffer of choice up to 72 hrs with at least 3 refills
4. Gradient cesium chloride ultracentrifugation at 150,000 g for 4-8 hrs at 4° C., expecting white film of phage near the 1.4 density layer.

Complexation of Phage with CNT and Dyes
1. CNT/phage complexes were fabricated as previously described in published work, Dang et al. Nature Nanotechnology 6, 377-384 (2011) with p8 coat protein insert sequence DSPHTELP selected for SWNT binding and pH control allowing for efficient dispersion of the complex.
2. Fluorescent dyes from the AlexaFlour NHS Ester line where picked for labeling of phage for imaging. The amine reactive chemistry of the dyes allows for easy labeling of side chains of lysine groups exposed by the p8 coat protein. Steps followed per manufacturer's instructions.
Labeled phage were processed under sterile conditions and dialyzed against buffer for 72 hrs before usage in vivo or in vitro studies.

In Vivo Imaging of Phage Complex in Mice
CNT complexed phage at varying concentrations [1e13, 6e13, 9e13 pfu/mL] and lengths [300, 880 nm] were prepared for 2004, tail vein injections in NCR-NU male mice (homozygous) post intracranial situation of glioma tumors. The mice were monitored post injection at 16 hr, 48 hr, 72 hr on the Belcher NIR-II Imager (setup at 808 nm laser, 2×1100 longpass, 2×1300 longpass, 1 second exposure). NIR-II imaging as previously described by Ghosh et al, PNAS 2014 111 (38) 13948-13953. At 71 hrs end of trial, mice were sacrificed and dissected and the brain was imaged for phage localization at the tumor site.

Chlorotoxin-expressing M13 Phage.
In Vitro Cellular Uptake Studies. Human U87MG glioblastoma cells were grown on glass coverslips coated with Poly-L-lysine (Gibco) in DMEM cell media (Corning) supplemented with 10% fetal bovine serum (Sigma). Human D458 medulloblastoma cells grown in suspension in DMEM/F12 media (Gibco) supplemented with 10% fetal bovine serum (Sigma), 1× Glutamax (Gibco), and 1× Pencillin/Streptomycin (Sigma). Cells were incubated at 37° C. with Cy5.5-conjugated CTX-expressing M13 phage for 6 hrs and 24 hrs. Coverslips with U87MG cells were washed three times with PBS before fixing with paraformaldehyde and processed for immunofluorescence. D458 cells were harvested into Eppendorf tubes, spun down at 1000 rpm×5 min, and washed three times with PBS before spinning onto glass microscope slides using a Shandon Cytospin (ThermoFisher). Immunofluorescence was performed on cells using Golgin 1 (Cell Signaling Technologies) as a Golgi marker, and DAPI (ThermoFisher) as a DNA stain for colocalization. Images were captured on an EVOS fluorescent microscope (Life Technologies) or a Nikon Eclipse 80i fluorescence microscope.

U87MG and GL261 Orthotopic Intracranial Tumor Implantation and In Vivo Tumor Monitoring. All animal experimentation was in adherence with the National Institutes of Health (NIH) Guide for the Care and Use of Laboratory Animals and received institutional approval. U87MG human glioma cells were purchased through ATCC (ATCC No. HTB-14) and maintained in DMEM media (Gibco) with 10% FBS (Hyclone). GL261 mouse glioma cells (Szatmari T et al, Cancer Sci, 2006, 97(6):546-553) were maintained in DMEM (Gibco) with 10% FBS (Hyclone), 1× Glutamine (Gibco), and 1× Pen/Strep (Sigma). Cell lines were transduced with a lentiviral pLMP-GFP-Luc vector to allow for stable expression of GFP and firefly luciferase prior to implantation. Six week old NCR nude (Taconic) or C57/BL6 male mice (Taconic) were used to generate intracranial orthotopic U87MG or GL261 gliomas, respectively. In brief, mice were anesthetized using 2% isoflurane and their heads immobilized in a stereotactic headframe using atraumatic ear bars. A burr hole was made using a steel drill bit (Plastics One, Roanoke, VA, USA) 1.4 mm right of the sagittal and 1 mm anterior to the lambdoid suture. 105 glioma cells were stereotactically injected 3 mm deep from the dura mater into the brain using a 33-gauge Hamilton syringe. Tumors were allowed to grow for 14 days prior to commencement of treatment. Intracranial tumor growth was monitored in vivo using bioluminescence IVIS® imaging (Xenogen, Almeda, CA) equipped with LivingImage™ software (Xenogen).

Multiphoton Intravital Imaging of In Vivo Tumor Uptake by Chlorotoxin-expressing M13 Phage Through A Cranial Window—To fashion a cranial window, the skull was thinned away using a sterile stainless steel 2 mm diameter cylindrical drill bit attached to a high-speed hand drill until the underlying dura mater is exposed. Multiphoton imaging was performed on an Olympus FV-1000MPE multiphoton microscope (Olympus Americas, Waltham, MA) using a 25×, N.A 1.05 water objective. Excitation was achieved using a DeepSee Tai-sapphire femtosecond pulse laser (Spectro-Physics, Santa Clara, CA) at 840 nm. The emitted fluorescence was collected by PMTs with emission filters of 425/30 nm for Collagen 1, 525/45 nm for GFP-labeled tumor cells and 668/20 nm for Alexa-647 nanoparticles. Collagen 1 was excited by second harmonic generation and emits as polarized light at half the excitation wavelength. Images were taken 24 hrs post-IV injection of Chlorotoxin-expressing M13 phage. All images were processed using Image."

REFERENCES

[1] Debadyuti, G., Kohli, A. G. et al. (2012). ACS Synthetic Biology 1(12): 576-582.
[2] Yi, H., Ghosh, D. et al. (2012). Nano letters 12(3): 1176-1183.
[3] Stroud, M. R, Hansen, S. J. et al. (2011). Current Pharm Des. 17(38): 4362-4371.
[4] Specthrie, L., Bullitt, E. et al. (1992). J Mol Biol 228(3): 720-724.
[5] Hewitt, J. A. (1975). Journal General Virology 26: 87-94.
[6] Griffith, J., Kornberg, A. (1974). Virology 59: 139-152.
[7] Smith, B. R., Kempen, P. et al. (2012). Nano Letters 12: 3369-3377.
[8] Gentile, F., Chiappini, C. et al. (2008). Journal of biomechanics 41(10): 2312-2318.
[9] Toy, R., Peiris, P. M. et al. (2014). Nanomedicine (Lond) 9(1): 121-134.
[10] Geng, Y., Dalhaimer, P. (2007). Nature Nanotechnology 2: 249-255.
[11] Veiseh, O., Sun, C. et al. (2009). Cancer Research 69(15): 6200-6207.
[12] Messing, J. (2016). Gene 683: 85-89.
[13] Krishnan, R., Tsubery, H. et al. (2014). J. Mol. Bio. 426: 2500-2519.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

All of the publications, patent applications and patents cited in this specification are incorporated herein by reference in their entirety to the same extent as if individually incorporated by reference.

What is claimed is:

1. A homogeneous engineered filamentous phage population, wherein at least 30% of filamentous phages in the phage population have a length within 15% of a selected length value, which is greater than the corresponding wild type filamentous phage length value and up to 10 microns.

2. The phage population of claim 1, wherein at least 50% of filamentous phages of the phage population have a length within 15% of the selected length value.

3. The phage population of claim 1, wherein at least 70% of filamentous phages of the phage population have a length within 15% of the selected length value.

4. The phage population of claim 1, wherein at least 90% of filamentous phages of the phage population have a length within 15% of the selected length value.

5. The phage population of claim 1, wherein the selected length value is from 900 nm to 10 microns.

6. The phage population of claim 1, wherein the selected length value is from 950 nm to 10 microns.

7. The phage population of claim 1, wherein the phage population has a count of at least 1e13 pfu.

8. The phage population of claim 1, further comprising an active agent attached to filamentous phages of the population, wherein the active agent is selected from a therapeutic agent, an imaging agent and a combination thereof.

9. The phage population of claim 8, wherein the active agent is an imaging agent.

10. The phage population of claim 9, wherein the imaging agent comprises a carbon nanostructure.

11. A therapeutic and/or imaging method comprising administering to a subject the homogenous engineered filamentous phage population of claim 8.

12. The method of claim 11 for treating and/or imaging a tumor.

13. The method of claim 12, wherein filamentous phages of the phage population comprise a tumor targeting moiety.

14. The method of claim 13, wherein the tumor targeting moiety comprises chlorotoxin.

15. The method of claim 14, wherein the chlorotoxin is a fluorescently labeled chlorotoxin.

16. The method of claim 14, wherein the tumor is selected from glioma, medulloblastoma, neuroblastoma, melanoma, primitive neuroectodermal tumor, and small cell lung carcinoma.

17. The method of claim 11, wherein the administering comprises intravascular administering.

18. The method of claim 11, wherein the administering comprises implanting the homogeneous engineered filamentous phage population.

19. The method of claim 18, wherein the said implanting is intracranial implanting.

20. A pharmaceutical composition comprising the homogeneous engineered filamentous phage population of claim 1.

21. An implant comprising the homogeneous engineered filamentous phage population of claim 1.

22. The implant of claim 21, which is one or more of a scaffold, a hydrogel or a nanostructure.

23. A phage comprising chlorotoxin expressed by a coat protein of the phage, wherein the phage is an engineered filamentous phage, which is a part of a homogeneous engineered phage population, wherein at least 30% of phages in the phage population have a length within 15% of a selected length value, which is greater than the corresponding wild type filamentous phage length value and up to 10 microns.

24. The phage of claim 23, wherein at least 50% of phages in the phage population have a length within 15% of the selected length value.

25. The phage of claim 23, wherein at least 70% of phages in the phage population have a length within 15% of the selected length value.

26. The phage of claim 23, wherein at least 90% of phages in the phage population have a length within 15% of the selected length value.

27. The phage of claim 23, further comprising an imaging agent.

28. The phage of claim 27, wherein the imaging agent comprises a carbon nanostructure.

29. The phage of claim 23, wherein the chlorotoxin is a labeled chlorotoxin.

30. The phage of claim 29, wherein the chlorotoxin is a fluorescently labeled chlorotoxin.

31. A pharmaceutical composition comprising the phage of claim 23.

32. An implant comprising the phage of claim 23.

33. The implant of claim 32, which is one or more of a scaffold, a hydrogel or a nanostructure.

34. A therapeutic and/or imaging method comprising administering to a subject the phage of claim 22.

35. The method of claim 34 for treating and/or imaging a tumor.

36. The method of claim 35, wherein the tumor is selected from glioma, medulloblastoma, neuroblastoma, melanoma, primitive neuroectodermal tumor, and small cell lung carcinoma.

37. The method of claim 34, wherein said administering is performed intravascularly.

38. The method of claim 34, wherein said administering is performed intracranially.

39. The method of claim 34, wherein said administering comprises implanting the phage.

40. The phage population of claim 1, which is a homogeneous engineered Ff phage population.

41. The phage population of claim 1, which is a homogeneous engineered M13 phage population.

42. The phage of claim 23, wherein the engineered filamentous phage is an engineered Ff phage.

43. The phage of claim 23, wherein the engineered filamentous phage is an engineered M13 phage.

* * * * *

SEQUENCE LISTING

```
<160> NUMBER OF SEQ ID NOS: 7

<210> SEQ ID NO 1
<211> LENGTH: 147
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
ttagtggtac ctttctattc tcactctatg tgcatgccgt gctttaccac cgatcatcag      60 atgcgcgca aatgcgatga ttgctgcggc ggcaaaggcc gcggcaaatg ctatggcccg     120
cagtgcctgt gccgctcggc cgaaact                                         147

<210> SEQ ID NO 2
<211> LENGTH: 95
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ccatcgccct gatagacggt ttttcgccct ttgacgttgg ctttaatagt ggactcttgt      60
tccaaactgg aacaacactc aaccctatct cgggc                                95

<210> SEQ ID NO 3
<211> LENGTH: 95
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ccatcgccct gatagacggt ttttcgccct ttgacgttgg ctttaatagt ggactcttgt      60
tccaaactgg aacaacactc aaccctatct cgggc                                95

<210> SEQ ID NO 4
```

```
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ggccatcgcc ctgatagacg gtttttcgcc ctttgacgtt ggagtccacg ttctttaata     60
gtggactctt gttccaaaca acact                                          85

<210> SEQ ID NO 5
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ggccatcgcc ctgatagacg gtttttcgcc ctttgacgtt ggagtccacg ttctttaata     60
gtggactctt aactggaaca acact                                          85

<210> SEQ ID NO 6
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
cgcgccctgt agcggcgcat taagcgcggc gggtgtggtg gttacgcgca gcgtgaccgc     60
tacacttgcc agcgccctag cgcccgctcc                                     90

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 7

His His His His His His
1               5
```